United States Patent
Benzel et al.

(10) Patent No.: US 10,304,563 B1
(45) Date of Patent: *May 28, 2019

(54) MEDICATION MANAGEMENT

(71) Applicant: TOUCHSTREAM CORP., Rochester, NY (US)

(72) Inventors: Joel Benzel, Pittsford, NY (US); Robert Gretzinger, Rush, NY (US)

(73) Assignee: TOUCHSTREAM CORP., Rochester, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/156,503

(22) Filed: Oct. 10, 2018

Related U.S. Application Data

(63) Continuation of application No. 14/451,022, filed on Aug. 4, 2014, now Pat. No. 10,133,848.

(60) Provisional application No. 61/862,140, filed on Aug. 5, 2013, provisional application No. 61/862,147, filed on Aug. 5, 2013.

(51) Int. Cl.
  *G06F 19/00* (2018.01)
  *G16H 20/10* (2018.01)
  *G16H 20/13* (2018.01)

(52) U.S. Cl.
  CPC .......... *G16H 20/13* (2018.01); *G16H 20/10* (2018.01)

(58) Field of Classification Search
  None
  See application file for complete search history.

(56) References Cited

U.S. PATENT DOCUMENTS

| | | |
|---|---|---|
| 6,771,174 B2 | 8/2004 | Broas |
| 7,946,101 B1 | 5/2011 | McGonagle et al. |
| 8,258,961 B2 | 9/2012 | Phillips et al. |
| 8,799,016 B1 | 8/2014 | Cohan et al. |
| 2002/0153411 A1 | 10/2002 | Wan et al. |
| 2005/0110640 A1 | 5/2005 | Chung |
| 2010/0185456 A1 | 7/2010 | Kansal |
| 2011/0119073 A1 | 5/2011 | Hanina et al. |
| 2011/0224501 A1 | 9/2011 | Hudsmith |

(Continued)

FOREIGN PATENT DOCUMENTS

WO  2009039124 A1  3/2006

OTHER PUBLICATIONS

Abrahms. "ORCATECH Living Laboratory." AARP Bulletin. Apr. 2012: 16-17.

(Continued)

*Primary Examiner* — Elaine Gort
*Assistant Examiner* — Devin C Hein
(74) *Attorney, Agent, or Firm* — Rossi, Kimms & McDowell LLP

(57) ABSTRACT

Medication management is facilitated at least by accessing at least a portion of data, the data may identify medication sets to be taken by a user according to a schedule including time periods. Each of the plurality of medication sets may be associated in the data with identification codes and at least one of the time periods. A medication message may be output identifying a particular medication set of the medication sets to be taken at a particular time period of the time periods. An input identification code may be received, and it may be determined whether the input identification code corresponds to the particular medication set. A warning message may be output in response to it being determined that the input identification code does not correspond to the particular medication set.

17 Claims, 17 Drawing Sheets

(56) References Cited

U.S. PATENT DOCUMENTS

| | | |
|---|---|---|
| 2011/0231202 A1 | 9/2011 | Hanina et al. |
| 2012/0131465 A1 | 5/2012 | Telek et al. |
| 2012/0179485 A1 | 7/2012 | Saneii |
| 2013/0002795 A1 | 1/2013 | Shavelsky et al. |
| 2014/0006040 A1 | 1/2014 | Apell et al. |
| 2014/0310018 A1 | 10/2014 | Cizmarik |

OTHER PUBLICATIONS

Abbott. "Independa Solutions Now Generally Available on Specially Designed TVs and Tablets." Independa Press Release. Jan. 9, 2013: 1-2, San Diego.

Office Action issued in U.S. Appl. No. 14/451,022 dated Dec. 15, 2016.

Office Action issued in U.S. Appl. No. 14/451,022 dated Jul. 25, 2017.

Office Action issued in U.S. Appl. No. 14/451,022 dated Dec. 18, 2017.

Notice of Allowance issued in U.S. Appl. No. 14/451,022 dated Aug. 24, 2018.

Office Action issued in U.S. Appl. No. 15/333,795 dated Dec. 16, 2016.

Office Action issued in U.S. Appl. No. 15/333,795 dated May 18, 2017.

Dayer et al., "Smartphone medication adherence apps: Potential benefits to patients and providers." Journal of the American Pharmacists Associates, 2013: 172-181, vol. 53, Issue 2.

Evening Medications — 330

Thu Jul 18 
6:00 – 6:30

Use Thurs PM Container — 332

Lucy — 334

- Metformin, 500 mg — 336A
  Do not crush or chew the tablet.    1 Tablets
- Tylenol, 500 mg — 336B
  Avoid other acetaminophen products.    1 Capsules
- Calcium Carbonate, 500 mg — 336C
  Take with a glass of orange juice.    1 Tablets © 2014 TouchStream Solutions, Inc.

Evening Medications

Thu Jul 18
6:00 — 6:30

Complete
615

Metformin, 500 mg — 1 Tablets
Do not crush or chew the tablet.

Tylenol, 500 mg — 1 Capsules
Avoid other acetaminophen products

Calcium Carbonate, 500 mg — 1 Tablets
Take with a glass of orange juice.

Lucy

I Did It

Close

© 2014 TouchStream Solutions, Inc.

MEDICATION MANAGEMENT

CROSS-REFERENCE TO RELATED APPLICATIONS

This application is a continuation of prior U.S. patent application Ser. No. 14/451,022, filed Aug. 4, 2014, which claims the benefit of each of U.S. Provisional Application No. 61/862,140, filed Aug. 5, 2013, and U.S. Provisional Application No. 61/862,147, filed Aug. 5, 2013, the entire disclosure of each of the applications cited in this section is hereby incorporated herein by reference.

COPYRIGHT NOTICE

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

TECHNICAL FIELD

Some embodiments of the present invention relate to medication management. For example, some embodiments of the present invention relate to a medication management system that includes or references medication identifiers or identification codes.

BACKGROUND OF THE INVENTION

Digital systems and devices which provide services to elderly clients are available from a number of companies. For example, Independa™, of San Diego, Calif., provides services to enable organizations and individuals to cost-effectively help the elderly remain independent longer by providing social engagement, medication and appointment reminders, and wireless health and safety monitoring. These features may be provided using a system which includes a TV or tablet computer located in the elder person's home. Aspects of this system are described in U.S. Patent Application Publication 2012/0179485 "Systems and Methods for Integrated Care Management" to Saneii.

A tablet computer, such as an Apple™ iPad™, is a one-piece mobile computer which uses a touch screen as the primary means of control. Tablet computers typically connect to the Internet using wireless communications technologies, such as WiFi or cellular data communications. Tablet computers can use "apps" to provide many different functions. For example, the RxmindMe™ Prescription/Medicine Reminder and Pill Tracker of Walgreens Co., 200 Wilmot Road Deerfield, Ill. 60015, is a prescription reminder that uses multitasking to alert the user when they need to take a prescription. It allows the user to enter all their prescriptions, setup reminders, and track when they have taken them.

In order to track whether users are taking their medication, a pillbox can be wired with sensors to create a "smart pillbox", as described in the article, "ORCATECH Living Laboratory", AARP Bulletin, pp. 16-17 (April 2012).

It is known to provide portable registration devices to assist in remote health care, as described in EP 2219515 "Method and System for Providing Remote Healthcare".

It is known to use RFID technology to identify storage containers, as described in U.S. Pat. No. 8,258,961 "RFID Reader Enclosure and Man-O-War RFID Reader System".

However, there remains a need in the art for improvements in the above-discussed technologies.

SUMMARY

At least the above-discussed need is addressed and technical solutions are achieved by various embodiments of the present invention. In some embodiments a method for providing medication management is executed by a system including an input-output device system; a processor-accessible memory device system; and a data processing device system communicatively connected to the processor-accessible memory device system and the input-output device system. The data processing device system is configured at least by a program stored in the processor-accessible memory device system at least to execute the method. The method may include accessing at least a portion of data. The data may identify a plurality of medication sets to be taken by a user according to a schedule including a plurality of time periods. Each of the plurality of medication sets may be associated in the data with at least one of a plurality of identification codes and at least one of the plurality of time periods. The method may also include causing the input-output device system to output a medication message which identifies a particular medication set of the plurality of medication sets to be taken at a particular time period of the plurality of time periods. The method may further include receiving, via the input-output device system, an input identification code, and determining whether the input identification code corresponds to the particular medication set based at least upon an analysis of at least a portion of the data and the input identification code. Also, the method may include causing the input-output device system to output a warning in response to it being determined that the input identification code does not correspond to the particular medication set.

In some embodiments, at least one of the plurality of medication sets includes only a single medication type. In some embodiments, at least one of the plurality of medication sets includes a plurality of medication types.

The input-output device system may include a reading device configured to read the input identification code from a medication.

In some embodiments, each of a plurality of medication containers includes a cavity for holding one of the medication sets. At least one of the medication containers may contain a liquid or cream medication. In some embodiments, the input-output device system includes a reading device configured to read the input identification code from one of the medication containers.

In some embodiments, the method includes causing the input-output device system to output the medication message as an audio message.

The system may be contained within a single housing encompassing a digital device.

In some embodiments, the data is stored in the processor-accessible memory device system.

In some embodiments, the method includes accessing, via the input-output device system, the at least the portion of the data from a network-accessible storage device system provided by a remote server.

The input-output device system may include a network interface communicatively connected to a network, and the method may include receiving, via the network and the network interface of the input-output device system, configuration instructions from a remote device; and configuring at least some of the data in accordance with the configuration instructions.

The input-output device system may include a network interface communicatively connected to a network, and the method may include establishing, via the network and the network interface of the input-output device system, a communicative connection with a remote device; and synchronizing at least some of the data with the remote device via the communicative connection.

In some embodiments, the input-output device system includes a network interface communicatively connected to a network, and the method includes transmitting, via the network and the network interface of the input-output device system, a warning message to a remote device in response to it being determined that the input identification code does not correspond to the particular medication set.

In some embodiments, the input-output device system includes a network interface communicatively connected to a network, and the method includes establishing, via the network and the network interface of the input-output device system, a communicative connection with a remote device in response to it being determined that the input identification code does not correspond to the particular medication set. The method may include establishing a video conference with the remote device via the communicative connection in response to it being determined that the input identification code does not correspond to the particular medication set.

In some embodiments, the user is a first user, and the method includes identifying that the input identification code is associated with a user other than the first user; and causing the input-output device system to output a message indicating an incorrect user in response to identifying that the particular user is other than the first user.

In some embodiments, the data identifies at least two different users and a plurality of medications to be taken by the at least two different users, and the method includes causing the input-output device system to output medication messages to each of the at least two different users.

In some embodiments, the medication message includes medication dosing instructions.

In some embodiments, the method includes receiving input confirmation indicating that the particular medication set has been taken by the user. The method may include modifying the data to account for the input confirmation. The modifying of the data may include modifying the data to include an indication of one or more medication dosages taken by the user and at what time or times.

In some embodiments, the method includes receiving, via the input-output device system, a second input identification code; prompting, via the input-output device system, for user-input information associated with an added medication corresponding to the second input identification code; receiving, via the input-output device system, the user-input information; and modifying the data to account for and associate the added medication, the second input identification code, and the user-input information.

In some embodiments, the method includes receiving, via the input-output device system, a second input identification code; determining that the second input identification code corresponds to an on-demand medication; and receiving input confirmation, via the input-output device system and in response to it being determined that the second input identification code corresponds to the on-demand medication, the input confirmation indicating that the on-demand medication has been taken by the user. The method may include causing the input-output device system to output dosing instructions for the on-demand medication in response to it being determined that the second input identification code corresponds to the on-demand medication. In some embodiments, the method includes causing data storage of an indication of the on-demand medication, a present dosage taken of the on-demand medication, and a time at which the present dosage of the on-demand medication was taken by the user, in response to receiving the input confirmation.

In some embodiments, the method includes receiving, via the input-output device system, a second input identification code; determining that the second input identification code corresponds to an on-demand medication; retrieving earlier dosages of the on-demand medication taken by the user within a time period; determining whether the earlier dosages of the on-demand medication taken by the user, if taken with an additional present dosage of the on-demand medication within the time period, would exceed a maximum dosage; and causing the input-output device system to output a warning message indicating excess medication dosage in response to it being determined that the maximum dosage would be exceeded.

In some embodiments a method for providing medication management is executed by a system including an input-output device system comprising a network interface configured to be communicatively connected to a network; a processor-accessible memory device system; and a data processing device system communicatively connected to the processor-accessible memory device system and the input-output device system. The data processing device system is configured at least by a program stored in the processor-accessible memory device system at least to execute the method. The method may include outputting, via the input-output device system, a schedule template for medications, the schedule template including a plurality of time windows. The method may include receiving, via the input-output device system, user-input associating particular medications with the time windows in the schedule template. The method may include generating a medication schedule for a particular user responsive to at least the user-input and storing the medication schedule in the processor-accessible memory device system. The method may include transmitting, via the network and network interface of the input-output device system, at least a portion of the medication schedule to a remote device; and receiving, from the remote device via the network and the network interface of input-output device system, an indication of the particular user taking a medication in accordance with the transmitted at least the portion of the medication schedule.

In some embodiments, the method includes receiving, via the input-output device system, second user-input pertaining to activities associated with the particular user; generating an activities calendar for the particular user responsive to at least the second user-input; storing the activities calendar in the processor-accessible memory device system; transmitting, via the network and the network interface of input-output device system, at least a portion of the activities calendar to the remote device; and receiving, from the remote device via the network and network interface of the input-output device system, an indication of the particular user completing an activity in accordance with the transmitted at least the portion of the activities calendar.

In some embodiments, the user-input includes an indication of a starting date and an ending date for one particular medication. The method may comprise including the particular medication in the medication schedule only during the period between the starting date and the ending date.

Any of the features of any of the methods discussed herein may be combined with any of the other features of any of the methods discussed in herein. In addition, a computer program product may be provided that comprises program code portions for performing some or all of any of the methods and associated features thereof described herein, when the computer program product is executed by a computer or other computing device or device system. Such a computer program product may be stored on one or more non-transitory computer-readable data storage mediums.

In some embodiments, each of any or all of the computer-readable data storage medium systems described herein is a non-transitory computer-readable data storage medium system including one or more non-transitory computer-readable data storage mediums storing one or more programs or program products which configure a data processing device system to execute some or all of one or more of the methods described herein.

For example, in some embodiments, a non-transitory computer-readable storage medium system comprises one or more non-transitory computer-readable storage mediums storing a program executable by one or more data processing devices of a data processing device system, the program including:

accessing instructions configured to cause accessing of at least a portion of data, the data identifying a plurality of medication sets to be taken by a user according to a schedule including a plurality of time periods, wherein each of the plurality of medication sets is associated in the data with at least one of a plurality of identification codes and at least one of the plurality of time periods;

first outputting instructions configured to cause an input-output device system communicatively connected to the data processing device system to output a medication message which identifies a particular medication set of the plurality of medication sets to be taken at a particular time period of the plurality of time periods;

receiving instructions configured to cause reception, via the input-output device system, of an input identification code;

determining instructions configured to cause a determination of whether the input identification code corresponds to the particular medication set based at least upon an analysis of at least a portion of the data and the input identification code; and second outputting instructions configured to cause the input-output device system to output a warning in response to it being determined that the input identification code does not correspond to the particular medication set.

For another example, in some embodiments, a non-transitory computer-readable storage medium system comprises one or more non-transitory computer-readable storage mediums storing a program executable by one or more data processing devices of a data processing device system, the program configured to cause the data processing device system to execute a method including:

outputting, via an input-output device system communicatively connected to the data processing device system, a schedule template for medications, the schedule template including a plurality of time windows;

receiving, via the input-output device system, user-input associating particular medications with the time windows in the schedule template;

generating a medication schedule for a particular user responsive to at least the user-input;

storing the medication schedule in a processor-accessible memory device system;

transmitting, via a network and network interface of the input-output device system, at least a portion of the medication schedule to a remote device; and receiving, from the remote device via the network and the network interface of input-output device system, an indication of the particular user taking a medication in accordance with the transmitted at least the portion of the medication schedule.

Further, any or all of the methods and associated features thereof discussed herein may be implemented as all or part of a device system or apparatus.

Various systems may include combinations or subsets of all the systems and associated features thereof described herein.

BRIEF DESCRIPTION OF THE DRAWINGS

It is to be understood that the attached drawings are for purposes of illustrating aspects of various embodiments and may include elements that are not to scale.

FIG. 6A-6F are examples of graphical user interface screens, according to some embodiments of the present invention;

FIG. 7A-7D are examples of graphical user interface screens, according to some embodiments of the present invention;

FIG. 8A depicts a weekly medication container assembly, according to some embodiments of the present invention.

DETAILED DESCRIPTION

Figure 1:
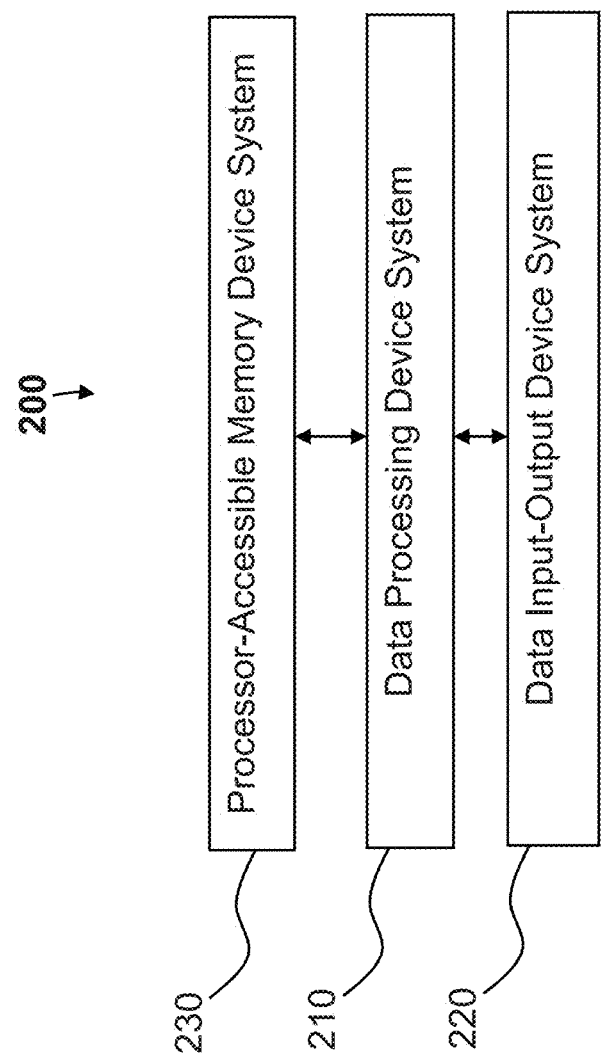
FIG. 1 illustrates a medication management system, according to some embodiments of the present invention.

In the following description, some embodiments of the present invention are described in terms that may be implemented at least in part as one or more software programs configured to be executed by a data processing device system. Some or all of such software programs may be equivalently constructed in hardware. Software and hardware not specifically shown, suggested, or described herein that is useful for implementation of any of various embodiments of the present invention are conventional and within the ordinary skill of the art.

In this regard, in the descriptions herein, certain specific details are set forth in order to provide a thorough understanding of various embodiments of the invention. However, one skilled in the art will understand that the invention may be practiced at a more general level without these details. In other instances, well-known structures have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least upon A' includes A as well as the possibility of one or more other additional elements besides A. In the same manner, the phrase, 'based upon A' includes A, as well as the possibility of one or more other additional elements besides A. However, the phrase, 'based only upon A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The term "program" in this disclosure should be interpreted as a set of instructions or modules that may be executed by one or more components in a system, such as a controller system or data processing device system, in order to cause the system to perform one or more operations. The set of instructions or modules may be stored by any kind of memory device, such as those described subsequently with respect to FIG. 1, FIG. 2, and FIG. 4. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). The word "module" may be defined as a set of instructions.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, the word "device", may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

FIG. 1 schematically illustrates a medication management system 200, according to some embodiments of the present invention. The system 200 may include a data processing device system 210, a data input-output device system 220, and a processor-accessible memory device system 230. The processor-accessible memory device system 230 and the data input-output device system 220 are communicatively connected to the data processing device system 210.

Figure 5:
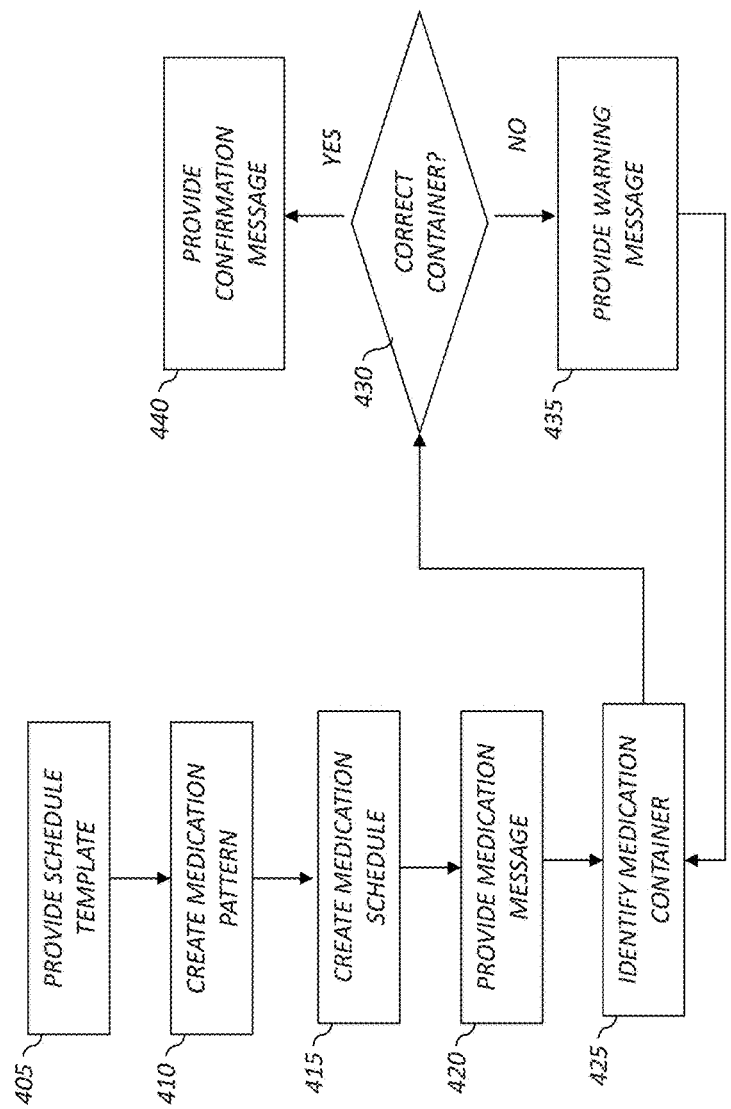
FIG. 5 illustrates a medication management method, which may be executed by the systems of any of FIG. 1, FIG. 2, or FIG. 4, according to some embodiments of the present invention.

The data processing device system 210 includes one or more data processing devices that implement or execute, in conjunction with other devices, such as those in the system 200, methods of various embodiments of the present invention, including the example methods of FIG. 5 described herein. Each of the phrases "data processing device", "data processor", "processor", and "computer" and the like is intended to include any data processing device, such as a central processing unit ("CPU"), a desktop computer, a laptop computer, a mainframe computer, a tablet computer such as an iPad™, a personal digital assistant, a cellular phone, a mobile device, a smart phone, or any other device for processing data, managing data, or handling data, whether implemented with electrical, magnetic, optical, biological components, or otherwise. In this regard, while some embodiments of the present invention are described herein in the context of one or more devices, such as a tablet computer, the invention is not so limited, and any other data processing device system may be used instead of or in addition to a tablet computer.

The processor-accessible memory device system 230 includes one or more processor-accessible memory devices configured to store program instructions and other information, including the information and program instructions needed by a data processing device system to execute the methods of various embodiments, including the example methods of FIG. 5 described herein. In this regard, each of the steps illustrated in the example methods of FIG. 5 may represent program instructions stored in the processor-accessible memory device system 230 and configured to cause a data processing device system to execute the respective step. The processor-accessible memory device system 230 may be a distributed processor-accessible memory device system including multiple processor-accessible memory devices communicatively connected to the data processing device system 210 via a plurality of computers and/or devices. On the other hand, the processor-accessible memory device system 230 need not be a distributed processor-accessible memory system and, consequently, may include one or more processor-accessible memory devices located within a single data processing device.

Each of the phrases "processor-accessible memory", "processor-accessible memory device", and the like is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, EEPROMs, and RAMs. In some embodiments, each of the phrases "processor-accessible memory" and "processor-accessible memory device" is intended to include or be a processor-accessible (or computer-readable) data storage medium. In some embodiments, each of the phrases "processor-accessible memory" and "processor-accessible memory device" is intended to include or be a non-transitory processor-accessible (or computer-readable) data storage medium. In some embodiments, the memory device system 230 may be considered to include or be a non-transitory processor-accessible (or computer-readable) data storage medium system. And, in some embodiments, the memory device system 230 may be considered to include or be a non-transitory processor-accessible (or computer-readable) storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the processor-accessible memory device system 230 is shown separately from the data processing device system 210 and the data input-output device system 220, one skilled in the art will appreciate that the processor-accessible memory device system 230 may be located completely or partially within the data processing device system 210 or the data input-output device system 220. Further in this regard, although the data input-output device system 220 is shown separately from the data processing device system 210 and the processor-accessible memory device system 230, one skilled in the art will appreciate that such system may be located completely or partially within the data processing system 210 or the processor-accessible memory device system 230, depending upon the contents of the input-output device system 220. Further still, the data processing device system 210, the data input-output device system 220, and the processor-accessible memory device system 230 may be located entirely within the same device or housing or may be separately located, but communicatively connected, among different devices or housings. In the case where the data processing device system 210, the data input-output device system 220, and the processor-accessible memory device system 230 are located within the same device, the system 200 of FIG. 1 may be implemented by a single application-specific integrated circuit (ASIC) in some embodiments.

The data input-output device system 220 may include a mouse, a keyboard, a touch screen, a computer, a processor-accessible memory device, a network-interface-card or network-interface circuitry, or any device or combination of devices from which a desired selection, desired information, instructions, or any other data is input to the data processing device system 210. The data input-output device system 220 may include a user-activatable control system that is responsive to a user action. The data input-output device system 220 may include any suitable interface for receiving a selection, information, instructions, or any other data from other devices or systems described in various ones of the embodiments.

The data input-output device system 220 also may include an image generating device system, a display device system, a reading device (such as a code scanner, RFID reader, camera, image scanner, or other reading device), an audio generating device system, an audio transducer, a computer, a processor-accessible memory device, a network interface (e.g., network interface card or network interface circuitry), or any device or combination of devices to which information, instructions, or any other data is output by the data processing device system 210. The input-output device system 220 may include any suitable interface for outputting information, instructions, or data to other devices and systems described in various ones of the embodiments. If the input-output device system 220 includes a processor-accessible memory device, such memory device may or may not form part or all of the memory device system 230.

The user interfaces of at least FIG. 6A, 6B, 6C, 6D, 6E, 6F, 7A, 7B, 7C, 7D or a combination thereof may be implemented as part of the data input-output device system 220, according to various ones of some embodiments of the present invention.

Figure 2:
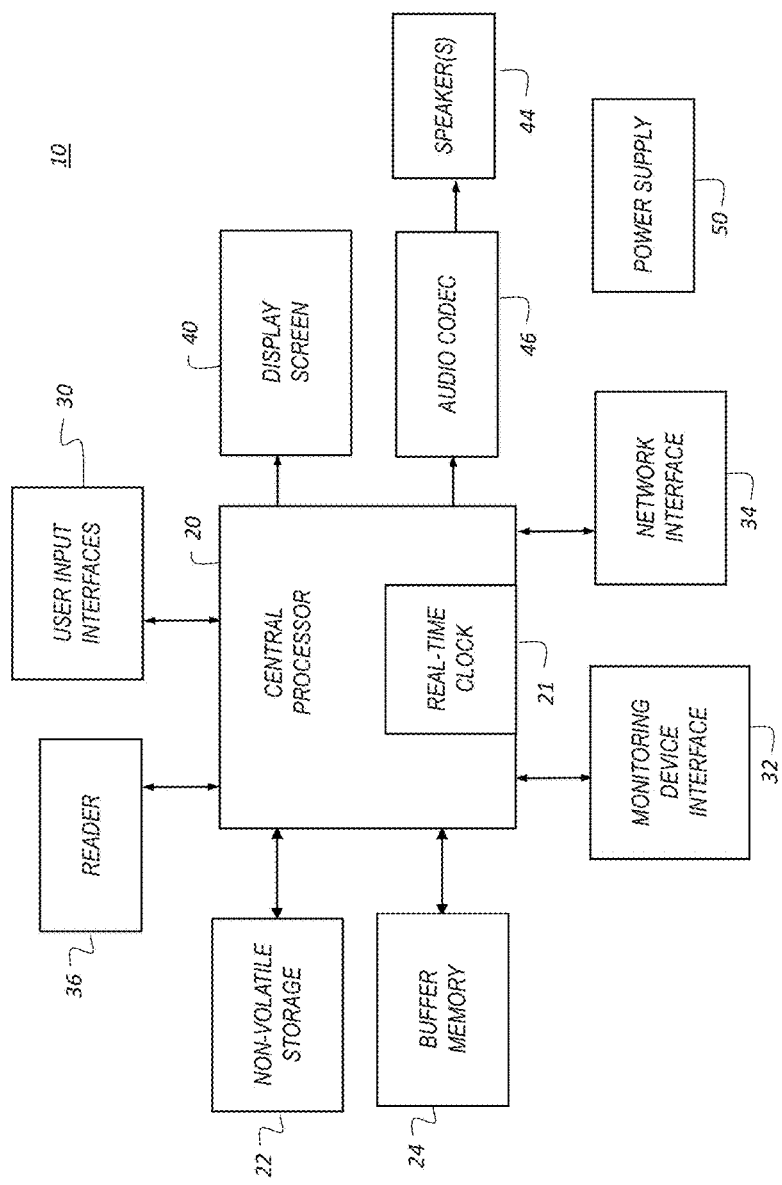
FIG. 2 illustrates a hardware configuration of a digital companion device, which may represent all or a portion of the system of FIG. 1, according to some embodiments of the present invention.

FIG. 2 is a high-level diagram depicting a digital companion device 10 according to some embodiments of the present invention. The embodiments of FIG. 2 represent one or more particular implementations of the medication management system 200 of FIG. 1. For example, the central processor 20, including its real-time clock 21, and the power supply 50 may be all or part of the data processing device system 210, according to some embodiments. The non-volatile storage 22, the buffer memory 24, or both, may be all or part of the processor-accessible memory device system 230, according to some embodiments. In some embodiments, the non-volatile storage 22, the buffer memory 24, or both, may be all or part of the data input-output device system 220. The reading device 36, the user input interfaces 30, the display screen 40, the audio codec 46, the speaker(s) 44, the network interface 34, and the monitoring device interface 32, may be all or part of the data input-output device system 220, according to some embodiments. All of the arrows in FIG. 2 represent communicative connections, according to some embodiments.

In some embodiments, the digital companion device 10 is a tablet computer running the Android operating system. Examples of other types of digital companion devices 10 that may be used in accordance with some various embodiments of the present invention include personal computers, hand-held computer (e.g., smart phones, PDAs, or digital media players) and digital televisions. In this regard, in some embodiments, the entire system 200 may be contained within a single housing encompassing a single digital device (e.g., a stand-alone device), such as a tablet computer, a hand-held computer, or digital television. However, as discussed above, the system 200, the digital companion device 10, or both need not be implemented by a single digital device contained within a single housing and, may, instead be implemented by more than one communicatively connected digital device. For a non-limiting example, the digital companion device 10 may be a stand-alone device that is communicatively connected to a remote server or remote server device system, according to some embodiments. According to at least some of these embodiments, the digital companion device 10 may be used by a patient, such as an elderly individual, on various medications, to, among other things, assist in the patient's medication-taking process, and the digital companion device 10 may, among other things, communicate statuses of the patient's medication-taking process to the remote server or remote server device system, which may, among other things, then inform a caregiver of the patient of such statuses.

Figure 3:
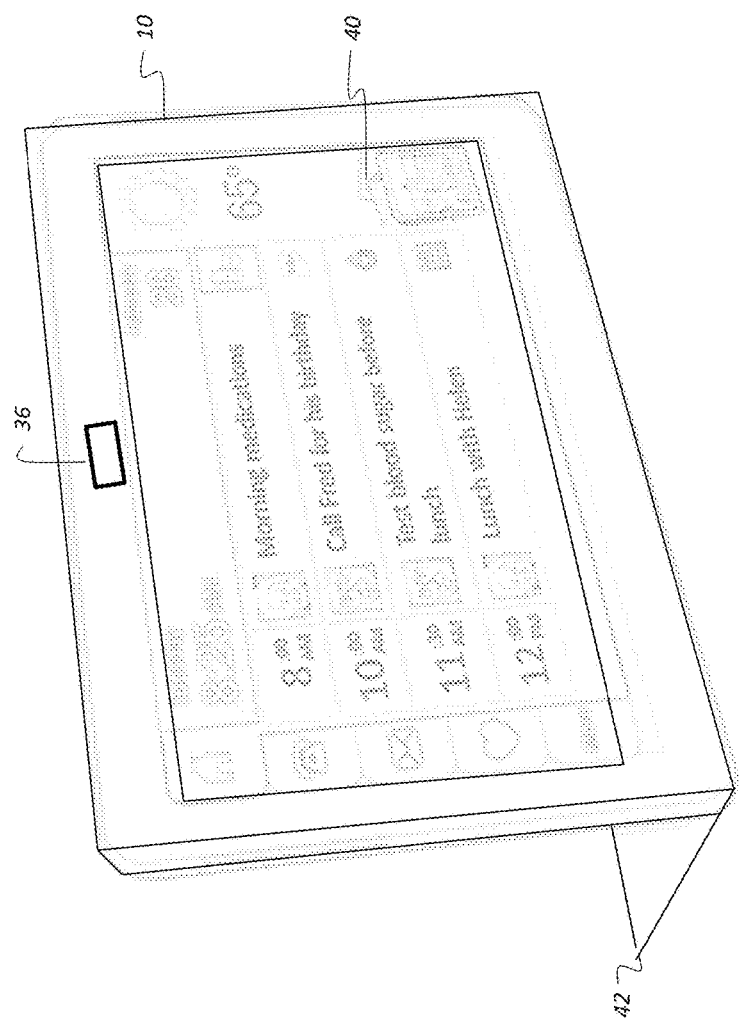
FIG. 3 depicts a front view of the digital companion device of FIG. 2, according to some embodiments of the present invention.

According to some embodiments, the digital companion device 10 may be configured by a caregiver and used by one or more home users associated with the caregiver. (It should be noted, however, that the present invention is not limited to any particular user or users, and, although the present specification refers to examples of caregivers and home users for simplicity of discussion, the present invention is not limited to users specifically responsible for caregiving or users operating a device at their home.) The home user or users may be an elderly individual or couple living in a home, an apartment, an independent living facility, or an assisted living facility. The caregiver may be a family member, such as a son, daughter, or grandchild, or a friend or health assistant. According to some embodiments, one function of the digital companion device 10 is to provide medication management for the home user(s). This medication management ensures that the home user(s) take(s) the proper medications at the proper times. The digital companion device 10 may be configured in conjunction with monitoring devices 102 (an example of which is shown in FIG. 3, according to some embodiments) to, among other things, measure the vital signs of the home user(s), and to help ensure their safety. The digital companion device 10 may be configured to confirm visits from individuals expected to provide assistance to the home user(s), who are assigned identification credentials 106 (shown in FIG. 4). These visits may include visits from medical personnel, elderly assistance personnel (e.g., "meals on wheels" drivers), housekeepers, and others who might visit the home user(s) on a regular basis.

According to some embodiments, the digital companion device 10 provides messages to the home user or users while requiring minimal user intervention. The messages may include visible messages, such as text, graphic images, video clips, or animations, or may include or additionally include audio information, such as speech, music, or sound effects. In some embodiments, the digital companion device 10 is configured to be used by multiple users, and messages for a particular user identify the user, for example by showing a picture of the user or by including the name of the user.

Referring again to FIG. 2, a central processor 20 in the digital companion device 10 provides the overall control of the digital companion device 10, according to some embodiments. The central processor 20 is coupled (that is, communicatively connected) to one or more user input interfaces 30, which enables a user of the digital companion device 10 to respond to messages and to select operating modes, according to some embodiments. The central processor 20 may be coupled to a monitoring device interface 32, which facilitates communication with various monitoring devices 102 (shown in FIG. 4) in the home. The central processor 20 may be coupled to a network interface 34, which facilitates communication with the internet 120 via an internet connection 110, which will be described later in reference to FIG. 4.

According to some embodiments, the central processor 20 is coupled to a buffer memory 24, which temporarily stores digital messages, such as digital images, for display on display screen 40. The central processor 20 may provide digital images to the display screen 40. The central processor 20 may be coupled to audio codec circuitry 46, which is configured to process digital audio information and convert the digital audio information to one or more analog signals, which may be provided to one or more speakers 44. It will be understood that speakers 44 are one type of audio output device. Other types of audio output devices may include an earpiece or hearing aid worn by the home user, and the invention is not limited to any particular audio output device.

The user input interface(s) 30 may be provided using various conventional user input devices and circuits. In some embodiments, the user input interface(s) 30 include a touch screen interface provided on the front surface of the display screen 40. In some embodiments, the touch screen interface is implemented using IR emitters and detectors in front of, and facing parallel to, the display screen 40.

In some embodiments, the user input interface(s) 30 may include buttons; switches; or a pointing device, such as a computer mouse, a joy stick, a track ball, or a track pad. In some embodiments, the user input interfaces 30 may include a remote control input device. The remote control may include user inputs which replicate some or all of the functions provided by the other user input interfaces 30, such as the touch screen or buttons. In some embodiments, the user input interfaces 30 may include a voice recognition interface (including a microphone and speech recognition processor) or a gesture recognition interface that includes a sensing device (such as a camera) which recognizes user hand gestures or other user movements, or a face recognition interface which recognizes the faces of particular users.

The central processor 20 may be coupled to a non-volatile storage or memory device 22, which may include, for example, flash EPROM memory which may serve as a program memory. In some embodiments, this program memory is communicatively connected to the central processor 20 and stores executable instructions, such as firmware programs, for controlling the operation of the central processor 20. In some embodiments, non-volatile storage 22 may also serve as a processor-accessible memory device for storing a medication schedule discussed in more detail below.

In some embodiments, the firmware programs stored in non-volatile memory 22 may be updated or replaced by new firmware provided by system management server 130 (shown in FIG. 4) using the network interface 34. In some embodiments, other types of non-volatile memory, such as Read Only Memory (ROM), magnetic disk storage or optical disc storage, may be used. In some embodiments, the central processor 20 includes an additional program memory (not shown), and the firmware programs stored in the non-volatile storage 22 are copied into the program memory before being executed by the central processor 20.

Figure 4:
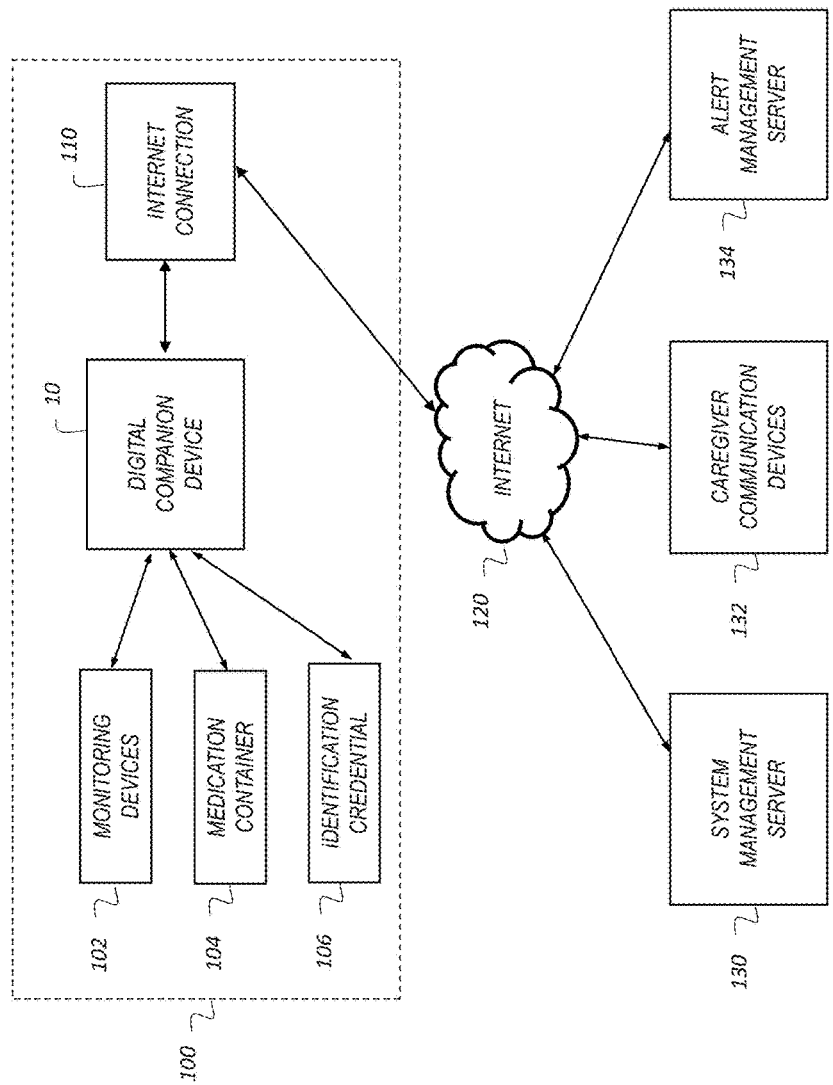
FIG. 4 illustrates a medication management system, which may be a particular implementation of the system of FIG. 1, according to some embodiments of the present invention.

According to some embodiments, the monitoring device interface 32 (FIG. 2) communicates with a variety of monitoring devices 102, shown in FIG. 4. The communications may be provided using a wireless or wired interface. In some embodiments, the monitoring device interface 32 uses a Bluetooth™ communications protocol to communicate with monitoring devices 102. In some embodiments, Z-wave™ or Zigbee™ communications is used instead of Bluetooth™, or in addition to Bluetooth™, to provide wireless communications. It will be understood that in some embodiments, the monitoring device interface 32 may use other wireless or wired communications protocols. In this regard, the arrows and FIG. 4 represent communicative connections, according to some embodiments.

The monitoring devices 102 can also include safety related devices such as a door monitor or door lock, a motion sensor, a panic button which can be operated by the home user in case of an accident, or a power control. The power control can be used, for example, to ensure that a coffee pot is not left on for longer than a predetermined time.

According to some embodiments, a reader or reading device 36 in the digital companion device 10 is configured to identify various objects, such as medication containers 104 and identification credentials 106, as will be described later in reference to FIG. 4. In some embodiments, the reader 36 is a RFID reader which is used to read information from RFID tags incorporated into the medication containers 104 and identification credentials 106. In some embodiments, the reader 36 is an optical reader which can read bar codes or other printed indicia on the medication containers 104 and identification credentials 106. In some embodiments, the reader 36 is an optical reader which identifies the medication using codes printed on the medication or the color, size, or shape of the medication. In some embodiments, the reader 36 is an optical reader which also identifies the particular user of the digital companion device 10 using face recognition. It will be understood that in some embodiments, the reader 36 can use other technologies, such as a magnetic reader to read data from a recorded magnetic strip located on the medication containers 104 and identification credentials 106.

The network interface 34 enables the digital companion device 10 to communicate over a network, such as the Internet. The network interface 34 may be configured as a wired interface, such as an Ethernet cable interface or a wired telephone modem. The network interface 34 may or may also be configured as a wireless interface, such as a WiFi (e.g., IEEE 802.11 WiFi standard) modem, a cellular modem, or a Bluetooth™ modem.

In some embodiments, the network interface 34 provides a direct connection to the Internet, and is configured to read HTML ("HyperText Markup Language") and to use TCP/IP ("Transmission Control Protocol/Internet Protocol"). In some embodiments, the network interface 34 provides a connection to a local area network, which may then provide an Internet connection using a wired or wireless router or other type of network interface device, which either interfaces directly to the Internet, or to an Internet Service Provider (ISP).

The display screen 40 may display images using a soft-copy display device, such as a color active matrix LCD ("Liquid Crystal Display"). In some embodiments, other soft-copy displays are used, such as an OLED ("Organic Light Emitting Diode") display, a CRT ("Cathode Ray Tube"), or various silicon-based displays. In some embodiments, the central processor 20 is connected to a TV signal output port, such as an HDMI port (not shown), which provides a signal for display on a display screen which is separate from the digital companion device 10, such as an HDTV display screen (not shown).

A power supply 50 may convert the AC power supplied via a wall plug (not shown) to the proper DC voltages needed to provide power to all of the components of the digital companion device 10. In some embodiments, the power supply may include a re-chargeable battery, so that the digital companion device 10 can be portable, thus allowing it to be used for a period of time without a connection to power.

The power supply 50 may include a power control circuit (not shown) which enables an active display mode for displaying messages and other information on the display screen 40, and a reduced power mode wherein the display screen 40 is turned off and does not display digital images. The power control circuit may be controlled by the central processor 20. The power control circuit may be configured to control the power to other portions of the digital companion device 10, such as audio codec 46, buffer memory 24, and monitoring device interface 32. In some embodiments, the digital companion device 10 may be configured by the caregiver to operate in the active display mode during certain hours (e.g., 7:00 AM to 9:00 PM each day), and otherwise to operate in the reduced power mode.

In some embodiments, the digital companion device 10 includes a motion sensor (not shown). The motion sensor may provide a signal to the central processor 20, which controls the power supply 50 in order to supply power to the display screen 40 only when motion is detected. This configuration reduces the power wasted when displaying images if there are no viewers in the vicinity of the digital companion device 10.

A real-time clock 21 in the central processor 20 provides a date/time of day value. In some embodiments, the real-time clock 21 is manually configured by the caregiver while in other embodiments, the real-time clock is configured using information accessed on an external device such as a Network Time Protocol (NTP) server using the network interface 34.

It will be understood that the functions of the central processor 20 may be provided using a single programmable processor or by using multiple programmable processors, including one or more digital signal processor (DSP) devices. Alternatively, the central processor 20 may be provided by custom circuitry (e.g., by one or more custom integrated circuits (ICs) designed specifically for use in digital devices, such as digital companion device 10), or by a combination of programmable processor(s) and custom circuits. It will be understood that connections between the central processor 20 and some of the components shown in FIG. 2 may be made using a common data bus. For example, in some embodiments some or all of the connections between the central processor 20, the non-volatile storage 22, the buffer memory 24, the monitoring devices interface 32, the reader 36, and the network interface 34 may be made using a common data bus.

FIG. 3 depicts a front view of the digital companion device 10, according to some embodiments. The digital companion device 10 may include a stand 42 which may be used to support the digital companion device 10 so that the display screen 40 is easily visible. The digital companion device 10 includes a reader 36 at the top middle, which is configured to read identification codes from the medication containers 104 and identification credentials 106 shown in FIG. 3. In some embodiments where the caregiver communication device 132 is the same as the digital companion device 10 or is the same type of device as the digital companion device 10, FIG. 3 may depict a front view of the caregiver communication device 132.

FIG. 4 is a high-level diagram depicting the medication management system 200, which includes a configuration where a system management server 130 is communicatively connected over a network to the digital companion device 10 and one or more caregiver communication devices 132 to provide medication management to home users, according to some embodiments of the present invention. It will be understood that a large number of digital companion devices 10, located at many different geographically dispersed locations, such as different houses or apartments in a community, may be supported by the system depicted in FIG. 4. In addition, it should be noted that although examples are provided herein with respect to particular configurations of the system management server 130, the one or more digital companion devices 10, and the one or more caregiver communication devices 132, the invention is not limited to such configurations, and such configurations may be more generally implemented by any particular device or combination of devices in accordance with the description of the system of FIG. 1. Although the digital companion device 10 is shown separately from the caregiver communication device 132 in FIG. 4, such devices may be the same device, according to some embodiments, although the configuration of FIG. 4 can have advantages in certain circumstances, e.g., where a company charges a fee for use of the system of FIG. 4 and such company may operate the system management server 130 distinctly from the digital companion device 10, which may be personally owned by the home user, and the caregiver communication device 132, which may be owned by the caregiver. The same applies with the system management server 130, where the digital companion device 10 and the system management server 130 could be the same device, according to some embodiments, or the caregiver communication device 132 and the system management server 130 could be the same device, according to some embodiments.

According to some embodiments, the digital companion device 10 communicates with a variety of monitoring devices 102, as described earlier in relation to FIG. 2. For example, the residence of the home user(s) may include several doors which are monitored, or locked and unlocked, using safety-related monitoring devices 102. The residence may include power controls which are used to control the power to a number of appliances, such as a coffee pot, iron, or toaster oven. The residence may include monitoring devices 102 which measure vital signs, such as a heart rate monitor, a blood pressure meter, or a scale to measure the weight of the home user.

According to some embodiments, the reading device 36 in the digital companion device 10 is configured to read information in order to identify medication containers 104. In this regard, the reading device 36 may be configured to read an identification code from one or more of the medication containers to input the identification code to the central processor 20. Each of one or more of the medication containers 104 may include a cavity for holding a single type of medication, e.g., many duplicate pills for a single prescription, or multiple types of different medications, e.g., one or more pills for each of a plurality of prescriptions, to be taken during a defined time period. However, the invention is not limited to pill-based medication or any other particular form of medication. In this regard, it will be understood that medication containers are not limited to holding pills, and in some embodiments may contain medications in the form of creams or liquids (e.g., sprays or drops). For example, the medication may take the form of eye drops, and the eye drop dispenser bottle may include an identification code, such as an RFID or bar code, which identifies the eye drop medication.

Because in some embodiments any particular medication container can contain one or more medications, it is sometimes referred to herein that a medication container includes a cavity for holding a medication set, where the medication set includes one or more medications.

It will be understood that medication containers may be provided in various sizes and shapes, and can utilize various materials, which can be, for example, transparent, semi-transparent, or opaque and which can also be, for example, either rigid, semi-rigid, or flexible. For example, a medication container could be a clear, flexible, Ziploc™ plastic bag, an opaque, semi-rigid cardboard box, or a prescription pill bottle.

FIG. 8A depicts an example of a simplified representation of a weekly medication container assembly 80, which may represent a conventional "pillbox", according to some embodiments, and which may be used to provide all of the medications to be taken by a home user during a one week period. The weekly medication container assembly 80 includes seven columns of removable medication containers, with one column for each day of the week. The weekly medication container assembly 80 includes four rows of removable medication containers corresponding to four different time periods including a morning time period 84A, a noon time period 84B, an evening time period 84C, and a bedtime time period 84D. The weekly medication container assembly 80 therefore holds a total of 28 removable medication containers, such as Thursday morning medication container 82.

It will be understood that weekly medication container assembly 80 could have a different number of daily time periods (e.g., only a morning time period and an evening time period), and that that a bi-weekly or monthly medication container assembly could be used instead of a weekly medication container assembly. It will also be understood that the medication containers could be permanently fixed in the container assembly, rather than being removable. It will also be understood that each medication container could be provided as a separable (e.g. perforated) section of a flexible plastic web which contains the medications for each daily time period for a set period of time (e.g. a month).

Each of the medication containers, such Thursday morning medication container 82, includes a cavity for holding medications (e.g., Avelox™, Calcium, Metformin, Prednisone, Tylenol, Vitamin B-12 and Vitamin D3) to be taken by the home user during a defined time period (e.g., Thursday morning), a cap that can be lifted to remove the medications, and an identification code (e.g., an RFID, 1-dimensional or 2-dimensional barcode adhered to an underside of the cap or other location of the medication container, or any other tagging technology known in the art) for identifying the day of the week and the defined time period. In some embodiments, the identification code also identifies the medication(s) within the medication container cavity, the particular user of the medication(s), or both. A user identification may be particularly helpful when the digital companion device 10 is used by multiple users in the same household.

As described earlier with reference to FIG. 2, in some embodiments the identification code may be provided using an RFID tag incorporated into each medication container. In some embodiments, the identification code may be provided using a bar code or other printed indicia on each of the medication containers, such as Thursday morning medication container 82. It will be understood that in some embodiments, the identification code may be provided using other technologies, such a recorded magnetic strip located on each of the medication containers.

Figure 8B:
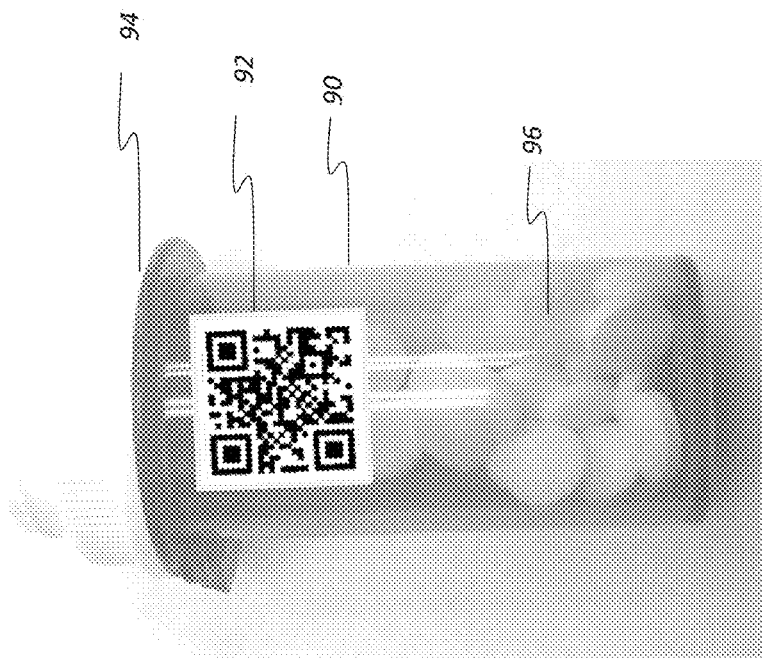
FIG. 8B depicts a single medication container, according to some embodiments of the present invention.

FIG. 8B depicts an example of a single stand-alone medication container 90. The medication container 90 includes a cavity 96 for holding a particular medication set (e.g., Calcium), a removable cap 94, which may be a child-proof cap, and an identification code 92, such as a bar code for identifying the particular medication set. It should be noted, however, that the invention may utilize any tagging technology known in the art for providing an identification code, even though FIG. 8B shows a 2-dimensional barcode.

According to some embodiments, the reader 36 in the digital companion device 10 shown in FIG. 2 is configured to read information in order to identify identification credentials 106 shown in FIG. 3. The identification credentials 106 may include, for example, ID badges worn by particular individuals and may include, for example, the name and photo of the individual. Each of the identification credentials 106 includes an identification code which may be configured to identify the particular individual providing assistance to the home user(s), or may be configured to identify the home user. The identification code may be provided, for example, using RFID tags incorporated into the identification credentials 106 or using bar codes or other printed indicia on identification credentials 106, or using other technologies, as described earlier at least in reference to FIG. 1.

In some embodiments, the identification credentials 106 may be used to confirm visits from particular individuals who provide assistance to the home user(s). These visits may include visits from medical personnel, elderly assistance personnel (e.g., "meals on wheels" drivers), housekeepers, and others who might visit the home user(s) on a regular basis. In some embodiments, the individual associated with the identification credential is asked to position the identification code near the digital companion device 10, so that the data confirming the time of his or her visit may be stored in a memory, such as non-volatile storage 22 or processor-accessible memory device system 230. This data may be used to update digital records associated with the home user(s), to confirm that they have received home care, meals, or medical attention on a particular day and time. It will be understood that the digital records associated with the home user(s) may be stored in a storage memory, such as non-volatile storage 22 in digital companion device 10, or using a network accessible storage system, such as a hard drive or other digital storage device (not shown) included with, or accessible by, system management server 130.

Returning to FIG. 4, the network interface 34 in the digital companion device 10 communicates over an internet connection 110 and the internet 120 to a system management server 130 according to some embodiments. In some embodiments, the internet connection 110 is provided by a wireless access point in the home user's residence. In some embodiments, the internet connection 110 is provided by a cellular data service using a modem located either in the digital companion device 10 or in a modem located in the home user's residence.

According to some embodiments, a system management server 130 is used by a caregiver to manage the medication related rules and behavior for one or more home users of the digital companion device 10. The system management server 130 may permit the caregiver to create a medication pattern for one or more home users, using his or her caregiver communication device 132, as will be described later in reference to FIG. 4.

The caregiver communication device(s) 132 may include any computer, for example, a smart phone or other mobile phone, a tablet computer, a portable computer, or a desktop computer.

The system management server 130 may be configured to communicate over the internet 120 with caregiver communication device(s) 132, in order to permit the caregiver to configure an account for one or more home users, and to manage the rules and behavior for the medication management to be provided to one or more home users.

In some embodiments, the system management server 130 stores one or more electronic addresses (e.g., an email address or a phone number) associated with the caregiver in a digital memory (e.g., a memory which may be accessed by the system management server 130, which may be all or part of the processor-accessible memory device system 230). The system management server 130 may be configured to send messages to the stored electronic address, which may be accessed by one or more of the caregiver communication devices 132 associated with a particular caregiver, in order to provide status or warnings concerning the particular home user, or users, for which they are caring. For example, if a home user does not acknowledge the completion of a scheduled activity, such as taking a medication, within a predetermined period, the system management servicer 130 may be configured to provide a warning message to the caregiver. This message may be provided, for example, as an email, SMS message, phone call, or any other type of electronic communication.

In some embodiments, the system management server 130 communicates over the internet 120 with an alert management system 134. The alert management system 134 may be configured to alert security personnel or medical personnel based on the rules provided by the caregiver and signals from monitoring devices 102. For example, in some embodiments the alert management system 134 is associated with a home security monitoring company, and the system management server 130 may alert the home security monitoring company, by communicating with the alert management server 134 if the home user has pressed a "panic" button on one of the monitoring devices 102, or if one of the monitoring devices 102 indicates that an exterior door of the home user's residence has been left open for an extended period of time.

In some embodiments, the system management server 130 performs some or all of the functions of alert management server 134. For example, the system management server 130 may be configured to provide an electronic message to the caregiver communication device(s) 132 associated with a particular home user, if the home user has pressed the "panic" button on one of the monitoring devices 102, or if one of the monitoring devices 102 indicates that one of the doors of the residence of the home user has been left open. In some embodiments, the caregiver communication device(s) 132 of the caregiver for a particular user may be used to remotely unlock the door of the residence of the home user, in order to allow access by emergency personnel.

In some embodiments, the system management server 130 or the alert management server 134 controls one of more of the monitoring devices 102, by communicating with the digital companion device 10 over the internet 120. For example, a door lock monitoring device may be unlocked at a particular time, to enable a particular individual providing assistance to the home user (such as a home care assistant or a meals-on-wheels driver) to enter the residence of the home user at a scheduled time, or to enable medical personnel or police to enter the residence if a "panic" button has been pressed on one of the monitoring devices 102.

It will be understood that in some embodiments, a residence may include two or more digital companion devices 10. For example, one digital companion device 10 may be located in a kitchen and a second digital companion device may be located in a bedroom or living room. The digital companion device 10 may include a motion sensor, or may communicate with motion sensor monitoring devices 102, to determine where the home user is located so as to conveniently provide information to the home user on the nearest digital companion device 10.

FIG. 5 is a high level flow diagram depicting a method for providing medication management, according to some embodiments of the present invention. This method may be executed by the system of FIG. 4 or the system of FIG. 1 under the direction of a program stored in a communicatively-connected processor-accessible memory device system.

In provide schedule template step 405, the system management server 130 provides a user interface to the caregiver communication device 132 to permit a caregiver to input medication information for one or more home users, according to some embodiments. This input may be accomplished, according to some embodiments, by the system management server 130 outputting, via a communicatively-connected data input-output device system (e.g., all or a portion of data input-output device system 220), a schedule template for medications to the caregiver communication device 132. The schedule template may include a plurality of time windows. For example, the schedule template may be configured to allow a user (e.g., a caregiver . . . note that the caregiver may be the home user him or herself in some embodiments) to define "time windows" during which the home user should take medications, including a group of unrelated medications, and permitting the caregiver to assign particular time periods to each time window. For example, the caregiver may assign the particular time period 8:00 AM to 8:30 AM to the "morning" time window, and assign two unrelated medications (e.g., Avelox™ and Melatonin) to the "bedtime" time window. In this regard, in some embodiments, the system management server 130 is configured to receive (e.g., from the caregiver communication device 132), via the communicatively-connected data input-output device system, user-input associating particular medications with the time windows in the schedule template.

Figure 6A:
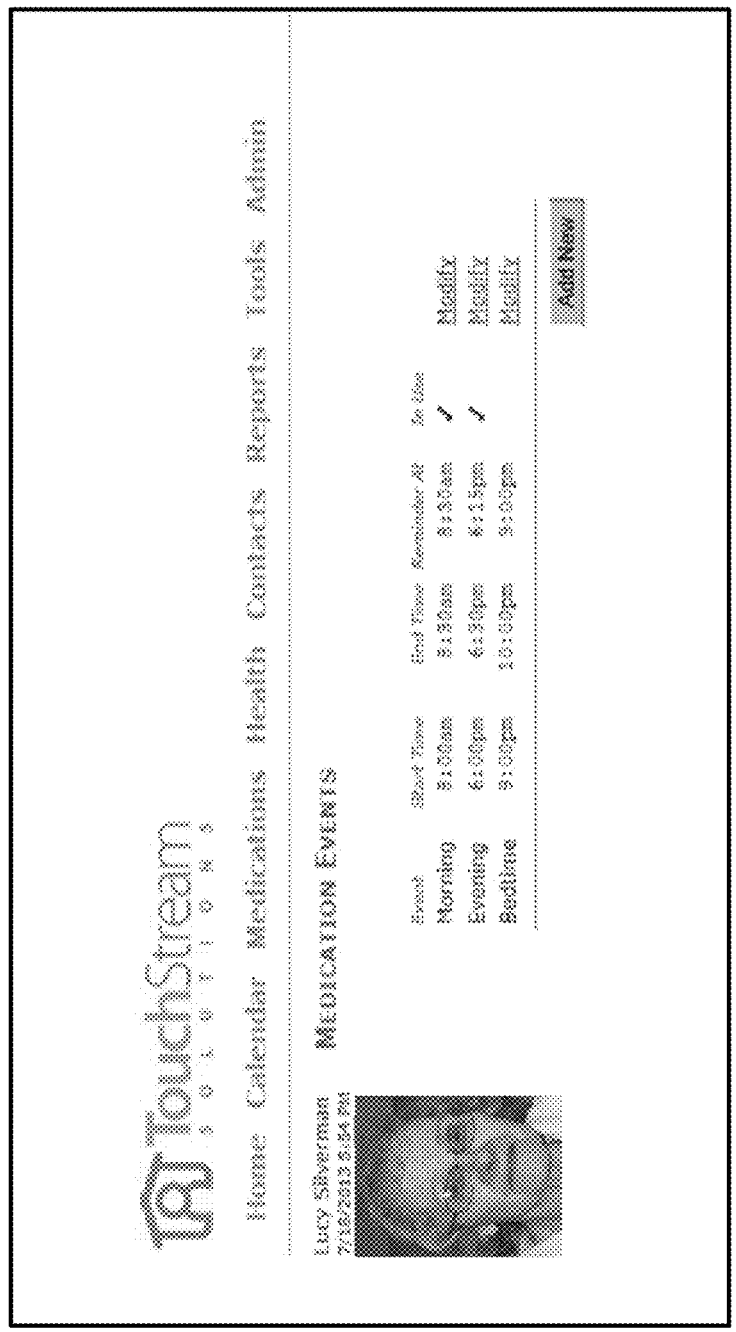

FIG. 6A is an example of a "medication events" user interface screen that may be provided, at least in part, by the system management server 130 via the internet 120 for display at a caregiver communication device 132 as part of step 405. The user interface screen of FIG. 6A is configured to receive input from a caregiver to specify time periods associated with the time windows during which the home user should be reminded to take medications, according to some embodiments. The time windows may be identified as "medication events" and may be scheduled at particular times of the day. For example, FIG. 6A depicts three time windows, including a morning medication event time window, which the caregiver has set to have a start time of 8:00 am and an end time of 8:30 am, an evening medication event time window, which the caregiver has set to have a start time of 6:00 pm and an end time of 6:30 am, and a bedtime medication event time window which the caregiver has set to have a start time of 9:00 pm and an end time of 10:00 pm. The caregiver may set "reminder" times for each medication event time window. Each of the medication event time windows may be modified by selecting the associated "modify" link. This modifying may include adding additional time windows (e.g., a "noon" time window) or deleting one or more particular time windows if it is foreseen that no medications will need to be taken during that particular time window. In some embodiments, time windows may be defined to be different for different days. For example, the "Morning" time window may be set from 8:00 am to 8:30 am for Monday-Friday, but may be 9:00 am to 9:30 am on Saturday and Sunday.

FIG. 6B is an example of a "modify medication event" user interface screen that may be provided as part of step 405, which is configured to receive user-input from a caregiver including a start time and end time of each medication event time window, in order to associate a particular time period (e.g., 8:00 am until 8:30 am) with a particular time window (e.g., the "morning" time window), according to some embodiments. The "modify medication event" user interface screen may be configured to allow selection of (a) whether or not the completion of the event should be tracked, (b) whether or not an alert should be sent to one of the caregiver communication devices 132, using the stored electronic address for the caregiver, as described earlier in relation to FIG. 4, or both (a) and (b).

Figure 6C:
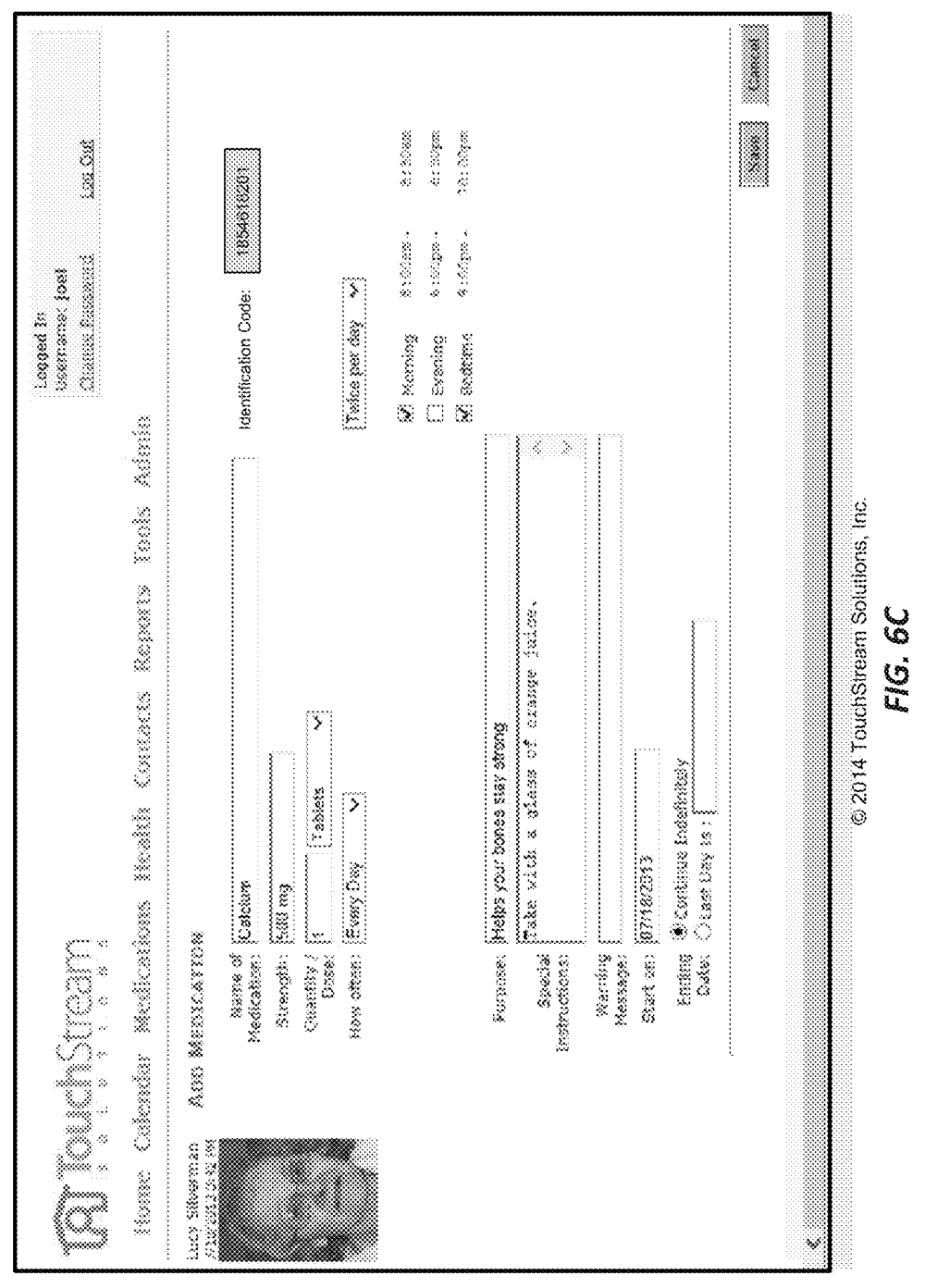

FIG. 6C is an example of an "add medication" user interface screen that may be provided as part of step 405, which is configured to receive user-input from a caregiver (e.g., username "joel") to input information about a particular medication (e.g., Calcium) to be taken by a particular home user (e.g., Lucy Silverman), according to some embodiments. In some embodiments, the user interface screen of FIG. 6C is configured to be presented in response to the user (e.g., the caregiver) reading (e.g., by way of a reading device like reader 36 in FIG. 2 communicatively connected to the caregiver communication device 132) an identification code (e.g., 92 in FIG. 8B) from a medication or medication container (e.g., 90 in FIG. 8B). For example, in embodiments where FIG. 3 depicts a caregiver communication device 132, the caregiver may place the barcode 92 in front of the reading device 36, which optically reads the identification code from the barcode 92 and transmits such code to the central processor 20, according to some of these embodiments.

In this regard, in some embodiments, the identification code may be distinct from (i.e., different than) a code (e.g., barcode) provided on a medication container by a manufacturer of the medication set or medication container, because such code provided on the medication container might not resolve to or otherwise particularly identify the medication set. Accordingly, in some embodiments, the identification code read by the reading device (e.g., 36 in FIG. 2 to cause the presentation of the user interface screen of FIG. 6C is defined (e.g., either by way of the user's data entry into the user interface screen of FIG. 6C or by predefinition, e.g., in a previously-produced catalog) to identify at least the medication set that is desired to be added, e.g., according to the user interface screen of FIG. 6C. In this regard, the universe of all identification codes that identify respective medication sets may be stored in one or more databases in a processor-accessible memory device system (e.g., 230 in FIG. 1 or a portion thereof) and accessible by the system of FIG. 4, FIG. 2, or FIG. 1. In some embodiments, such identification codes are stored as part of the medication schedule discussed below.

In some embodiments, multiple identification codes may be associated with a single medication, and all of such identification codes may be displayed on the screen of FIG. 6C. For example, as discussed above with respect to FIG. 8A, each identification code may be associated with a particular day of the week and defined time period for a particular medication set. For instance, the same medication set taken Tuesday Morning and Thursday Morning may have different identification codes for the Tuesday Morning set and the Thursday Morning set, so that the system is later able to know that the home user is not only taking the right medication set, but is also taking the right medication set for the right time period. Also as discussed above with respect to FIG. 8A, each identification code may also identify the particular user of the medication set. Accordingly, in some embodiments, the user interface screen of FIG. 6C may be configured to allow the caregiver to change the user associated with the newly added medication (e.g., from Lucy to someone else).

Upon receipt of the input identification code (sometimes referred to herein as a "second input identification code") via an input-output device system (e.g., all or a portion of 210 in FIG. 1, such as a reading device like reader 36 in FIG. 2), the data processing device system 210 or portion thereof of the caregiver communication device 132 is configured, according to some embodiments, to present the user, via the input-output device system (e.g., by a display device like display screen 40 in FIG. 2) with the user interface screen of FIG. 6C as a blank template with blank data fields, except for the identification code data field (shown to the right of the "name of medication" data field in FIG. 6C), which may display the input identification code read by the reading device in a manner not editable by the user (i.e., as represented with the grey background in the identification code data field in FIG. 6C). This blank template state of the user interface screen 605 prompts the user for user-input information associated with the medication set to be added, which corresponds to the input identification code. Then, according to some embodiments, the user interface screen of FIG. 6C is configured to permit the caregiver to enter the name of the medication set, the strength and quantity of the dosage(s) to be taken, and to allow selection of the time window(s) during which the medication set should be taken, all in association with the input identification code. This configuration enables the caregiver (e.g., Joel) who is associated with the particular home user (e.g., Lucy Silverman) to associate particular medication sets (e.g., calcium in the example of FIG. 6C), by way of the medication set's associated identification code, with particular time windows (e.g., morning and bedtime) in the schedule template described in relation to FIG. 6A. This information, upon receipt of it by the caregiver communication device 132 via its input-output device system (e.g., 220 in FIG. 1) is used in to generate a new or modify an existing medication pattern and medication schedule (e.g., create medication pattern step 410 and create medication schedule step 415 in FIG. 5) to account for and associate the added medication, the input identification code, and the user-input information (e.g., the information in the data fields shown in FIG. 6C) for the particular home user (e.g., Lucy Silverman), according to some embodiments.

Although the example user interface screen shown in FIG. 6C is shown for entry of information associated with a single medication, it may be configured to associate such information with plurality of medications. For example, there may be multiple "name of medication" fields with respective multiple strength and quantity/dose fields, all of which may be associated with a same identification code, same time windows (e.g., Morning, Evening, Bedtime), same dosage frequencies (e.g., "How often:"), same purpose, same special instructions, same warning, same start date, and same ending date shown in FIG. 6C, according to some embodiments.

The "Add medication" user interface screen shown in FIG. 6C may be configured to receive special instructions (e.g., by way of the "Special Instructions" text box in FIG. 6C) associated with the medication, such as dosage instructions or instructions on how to take the medication, according to some embodiments. These special instructions may be displayed to the home user on the digital companion device 10 at the time at which the home user is scheduled to take the medication. For example, if the medication is a cream or spray, the special instruction can describe where to apply the cream or spray, and how much cream or spray to use. The "Add medication" user interface screen shown in FIG. 6C may be configured to receive a user-defined warning message (e.g., by way of the "warning message" text box in FIG. 6C) associated with the medication. This warning message may be presented to the home user at the time at which the home user is scheduled to take the medication, or at another pre-defined time or under certain pre-defined circumstances.

The "Add medication" user interface screen shown in FIG. 6C may be configured to input a particular starting date and ending date for the medication. For example, a new medication may be prescribed for only a limited period (e.g., one week, or one month) to treat a particular illness. In this regard, the user-input received by the system management server 130 by way of the caregiver interaction with the user interface screen of FIG. 6C may include an indication of a starting date and an ending date for a particular medication, and the system management server 130 is configured (e.g., at least by a program) to include the particular medication in the medication schedule (step 415, discussed below) only during the period between the starting date and the ending date.

It will be understood that additional user interface screens (not shown) may be provided as part of step 405 to receive user-input to input information for medical related monitoring activities that should be performed on a regular basis. These activities may include, for example, reminders to the home user to measure his or her blood pressure, to test his or her blood sugar level at particular times or the day, or to measure his or her weight on particular days of the month.

It will be understood that additional user interface screens (not shown) may be provided as part of step 405 to receive user-input to input information to remind the home user of other scheduled activities. With this information, according to some embodiments, the server management server 130 generates an activities calendar for the particular home user, to remind the user of scheduled activities using messages provided by the digital companion device 10. The scheduled activities may include, for example, reminders to the home user to bring in the mail at a particular time of the day, or to take out garbage for pickup on a particular day of the week. The scheduled activities may include reminders of the times of favorite daily activities (e.g., favorite radio programs or TV shows). In some embodiments, the digital companion device 10 may be configured to allow viewing of the TV show or listening to the radio program, using a built-in radio receiver or TV tuner, or by receiving the program via the internet 120. In this regard, in some embodiments, the system management server 130 is configured to receive, via a communicatively connected input-output device system, user-input (e.g., "second" user-input, if user-input pertaining to the home user's medications is considered "first" user-input) pertaining to activities associated with a particular home user. In some embodiments, the system management server 130 configured to generate an activities counter for the particular home user responsive to at least the user-input pertaining to the activities associated with the particular home user. The system management server 130 may be configured to store the activities calendar in a communicatively-connected processor-accessible memory device system. With such an activities calendar, the system management server 130 may be configured to transmit, e.g., via a network interface and via the Internet 120 (or other network) at least a portion of the activities calendar to the digital companion device 10 (or other device associated with the home user or even associated with the caregiver). In some embodiments, the digital companion device 10 (or other device associated with the home user or even associated with the caregiver) may be configured to transmit (e.g., to the system management server 130 or another device, which may be associated with the home user or caregiver) an indication of the particular home user completing an activity in accordance with the transmitted at least the portion of the activities counter.

Figure 6D:
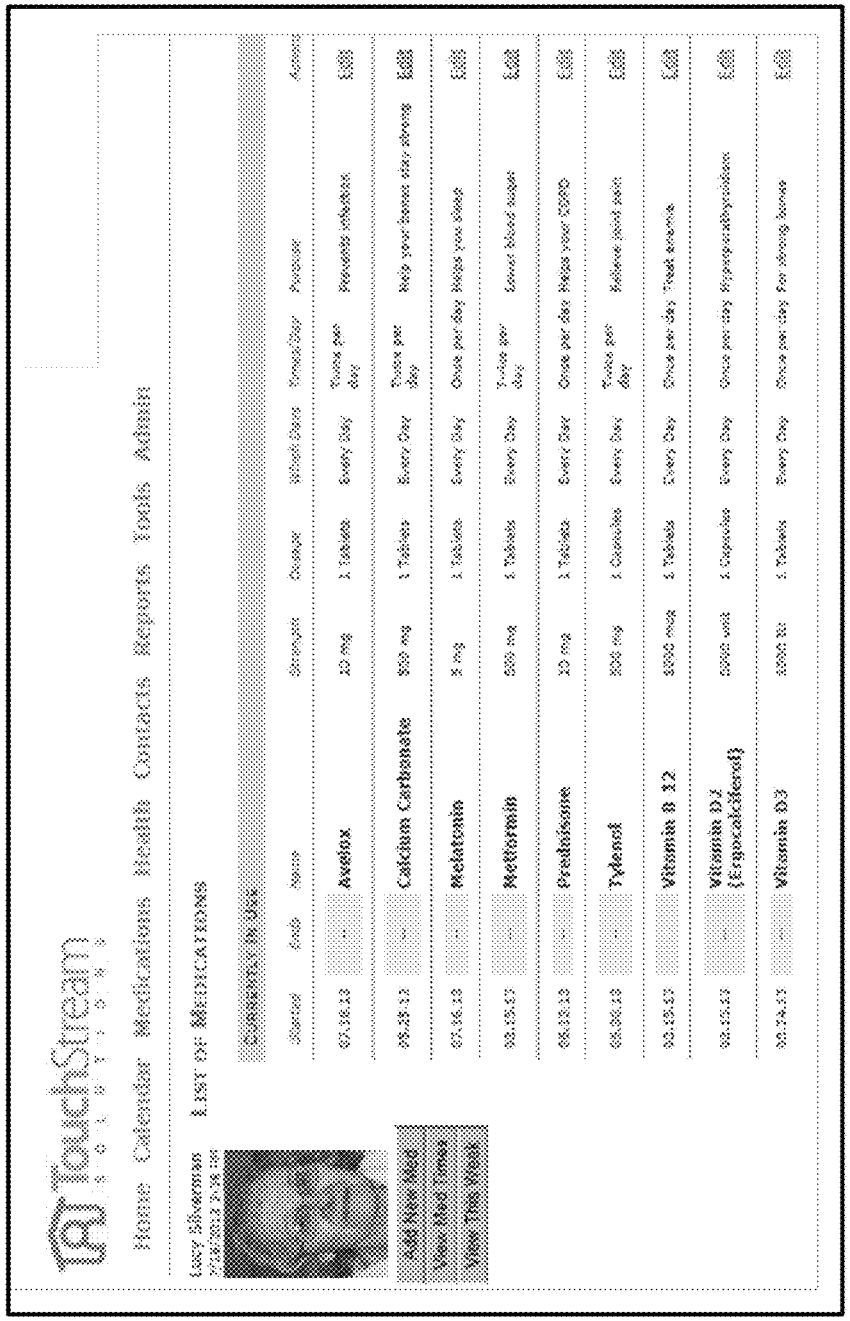

FIG. 6D is an example of a "list of medications" user interface screen that may be provided, at least in part, by the system management server 130 via the internet 120 for display at a caregiver communication device 132. According to some embodiments, this user interface is configured to present to the caregiver a review of the medications to be taken by the home user whose care he or she is managing. According to some embodiments, this user interface displays the names of the medications to be taken, along with the strength, dosage, days taken, times/day, and purpose. According to some embodiments, this user interface is configured to allow the caregiver to modify the displayed information using the edit link following each medication in the list.

Figure 6E:
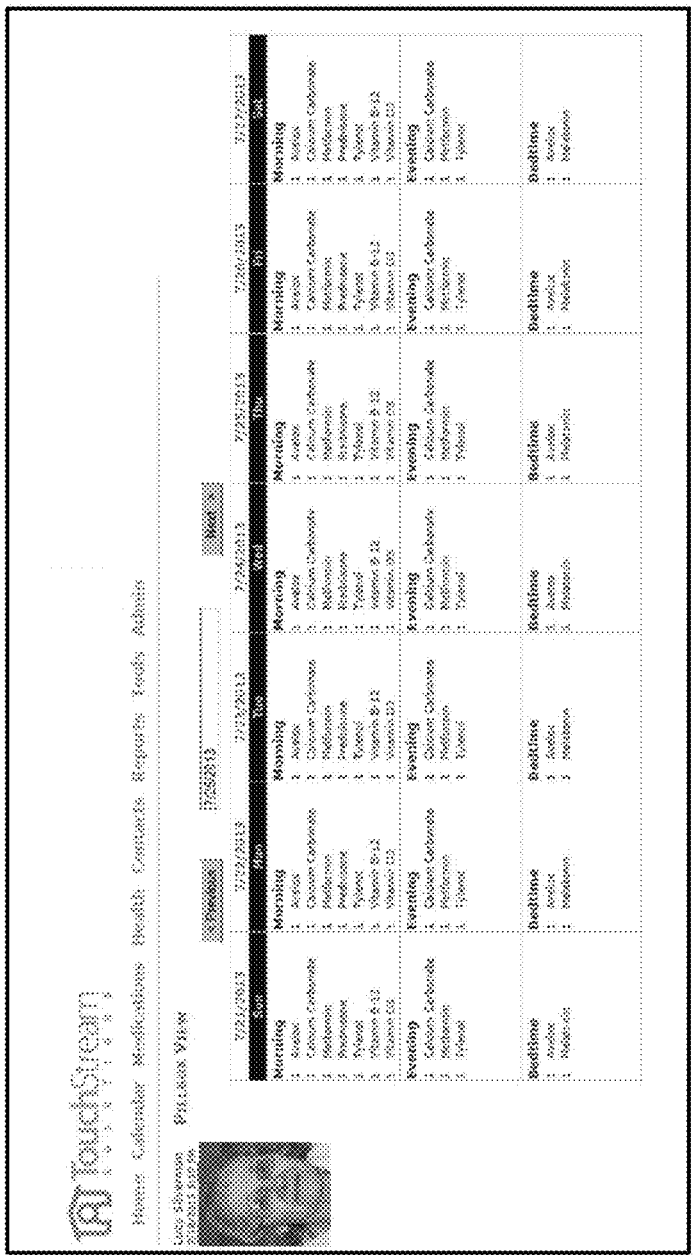

In create medication pattern step 410 of FIG. 5, a medication pattern is generated by the system management server 130 for the home user. This medication pattern may be displayed for review by the caregiver, as will be described with reference to the example of FIG. 6E. FIG. 6E is an example of a "pillbox view" user interface screen that may be provided, at least in part, by the system management server 130 via the internet 120 for display at a caregiver communication device 132. According to some embodiments, this user interface is configured to display a medication pattern. The medication pattern may include the medication event time windows (e.g., morning, evening, and bedtime) described earlier in relation to FIG. 6A for each day of the week, as well as the medications to be taken by the home user (e.g., Lucy) in each respective time window for each day, as defined according to the "Add Medication" user interface screen of FIG. 6C, discussed above. Accordingly, in some embodiments, the data processing device system 210 (or portion thereof) of the system management server 130 is configured to generate the medication pattern at least by compiling and organizing the user-input from at least the user interface screens of FIGS. 6A-6C. The "pillbox view" user interface screen of FIG. 6E is configured to guide the loading of a pillbox for the home user, according to some embodiments, where each day/time-window cell in FIG. 6C corresponds to a container in a pillbox. For example, the "Thursday morning" container 82 in FIG. 8A would be loaded with one tablet each of Avelox™, Calcium Carbonate, Metformin, Prednisone, Tylenol, Vitamin B-12, and Vitamin D3.

In create medication schedule step 415 of FIG. 5, a medication schedule is generated for the home user. In some embodiments, the medication schedule is generated by the system management server 130 in response to at least the user-input received by the data processing device in response to step 405 (e.g., via the user interfaces of FIGS. 6A-6C). In this regard, in some embodiments, the medication schedule may be the medication pattern generated at step 410 (e.g., FIG. 6E), a portion thereof, or an alternate representation of all or a portion of the medication pattern.

In this regard, steps 410 and 415 may be the same step in some embodiments. In some embodiments, the medication schedule may be a superset of the information presented in the "pillbox view" user interface screen of FIG. 6E, and, therefore, in some embodiments, the create medication schedule of step 415 and the create medication pattern step 410 may have swapped positions in FIG. 5, such that the medication schedule is generated first, and the "pillbox view" user interface screen of FIG. 6E is generated from the medication schedule.

In some embodiments, the medication schedule is represented by data that identifies a plurality of medications sets to be taken by a user (e.g., "Lucy" in FIG. 6E) according to a schedule (e.g., a portion of which is shown in FIG. 6E) including a plurality of time periods (e.g., each date/time-window cell in FIG. 6E). In some embodiments, each of the plurality of medications sets (e.g., calcium in FIG. 6C as an example of a medication set) is associated in the medication schedule data with at least one of a plurality of identification codes (e.g., the identification code shown in FIG. 6C) and at least one of the plurality of time periods (e.g., the checked "Morning" and "Bedtime" check-boxes in FIG. 6C). Accordingly, in some embodiments, at least one of the plurality of medication sets comprises only a single medication type (e.g., calcium). In some embodiments, medications are prescribed or otherwise provided in groups of a plurality of different medication types to be taken together are, e.g., provided in the same medication container. For example, the medications Avelox™ and Melatonin for the bedtime time window on Sunday in FIG. 6B may be provided in a single medication container with a single identification code provided therewith or thereon, such that the medications Avelox™ and Melatonin for the bedtime time window on Sunday in FIG. 6B are considered a single medication set comprising a plurality of medication types (e.g., Avelox™ and Melatonin in this example). In this regard, different medication types may be considered to be different medicines in some embodiments. In some embodiments, a group of multi-medication-type medication containers, each one for each time period, may be provided by a pharmacy as a plastic web. Each multi-medication-type medication container in the web may be separated from the remaining multi-medication-type medication containers in the web using perforations. The web of multi-medication-type medication containers provides a plurality of medication sets using the multi-medication-type medication containers, and each multi-medication-type medication container may include its own identification code which identifies the respective medication set corresponding to a particular time period.

In some embodiments, the data representing the medication schedule accommodates multiple home users, e.g., data describing at least that shown in the table of FIG. 6E along with respective medication set identification codes for each of a plurality of different users, where each of the different users has a portion of the medication schedule data defining his or her own medication sets, respective identification codes, respective dosages, time windows, and schedule. For example, in some embodiments each of the different users is provided with a different web of multi-medication-type medication containers, and the identification codes on each of the multi-medication-type medication containers in each of the webs is associated with a particular user as well as a particular time period. In some embodiments, the web of multi-medication-type medication containers for each user is identified using a particular color (e.g. Red), name (e.g. Lucy), or image (photo of Lucy) printed on the multimedication-type medication containers, and the messages provided by the digital companion device 10 identify the user (e.g. Lucy) and the multi-medication-type medication container identifier (e.g. "detach the next multi-medication-type medication container from the Red colored multi-medication-type medication container web".

The generated medication schedule is stored by the data processing device system 210 portion of the system management server 130 in a communicatively connected processor-accessible memory device system. In some embodiments, at least a portion of the data representing the medication schedule is stored in or in a portion of the processor-accessible memory device system 210 (FIG. 1) within at least (a) the housing of the system management server 130, (b) a housing of a digital companion device 10, (c) a housing of a caregiver communication device 132, (a) and (b), (a) and (c), (b) and (c), or (a), (b), and (c). In some embodiments where multiple devices store some or all of the data representing the medication schedule (e.g., when multiple digital companion devices 10, caregiver devices 132, or multiple digital companion devices 10 and caregiver devices 132 are communicatively connected, e.g., within a single household or otherwise), synchronization, using any technique known in the art, among such devices may be performed. For example, the data processing device system 210 or a portion thereof of the system management server 130, a digital companion device 10, or a caregiver communication device 132 may be configured to establish, via a network (e.g., the Internet 120) and a network interface of the respective input-output device system 220 or portion thereof, a communicative connection with a remote device (e.g., another computer of the system management server 130, another digital companion device 10, or another caregiver communication device 132) for synchronization of at least some of the medication schedule data.

From the perspective of the digital companion device 10, if at least a portion of the data representing the medication schedule is stored in a local processor-accessible memory device system within the housing of the digital companion device 10, the receipt of the at least the portion of the data representing the medication schedule by the digital companion device 10 may be considered a receipt of configuration instructions from a remote device (e.g., the system management server 130). In other words, the downloading of at least a portion of medication schedule data by the digital companion device 10 allows the digital companion device 10 to configure or update or modify a previous version of the medication schedule data stored by the digital companion device 10. In this regard, any of the data input via the user interface screens of FIGS. 6A-6C may be considered configuration instructions by which medication schedule data is configured, according to some embodiments.

From the perspective of the digital companion device 10, if at least a portion of the data representing the medication schedule is stored in a local processor-accessible memory device system within the housing of the digital companion device 10, the data processing device system 210 or a portion thereof (e.g., central processor 20) of the digital companion device 10 may be configured to access the at least the portion of such data from the local processor-accessible memory device system.

If at least a portion of the data is stored in a network-accessible storage device system provided by a remote server (e.g., is stored in a processor-accessible memory device system of the system management server 130), the data processing device system (e.g., central processor 20) of the digital companion device 10 may be configured to access the at least the portion of such data from the network-accessible storage device system provided by the remote server via a network interface (e.g., 34 in FIG. 2) of the input-output device system (e.g., 220 in FIG. 1) of the digital companion device 10.

In some embodiments, the medication schedule may be automatically generated or updated on a daily basis (e.g., each morning at 1:00 am) responsive to the medication pattern which has been input by the caregiver, as reflected in the pillbox view depicted in FIG. 6E for that particular day. It will be understood that in some embodiments, the medication schedule may be automatically generated or updated on a weekly or monthly basis, or may be generated or updated at the start of each medication event or when a new medication is added (e.g., the user interface screen of FIG. 6C) or information associated with an existing medication is changed.

Figure 6F:
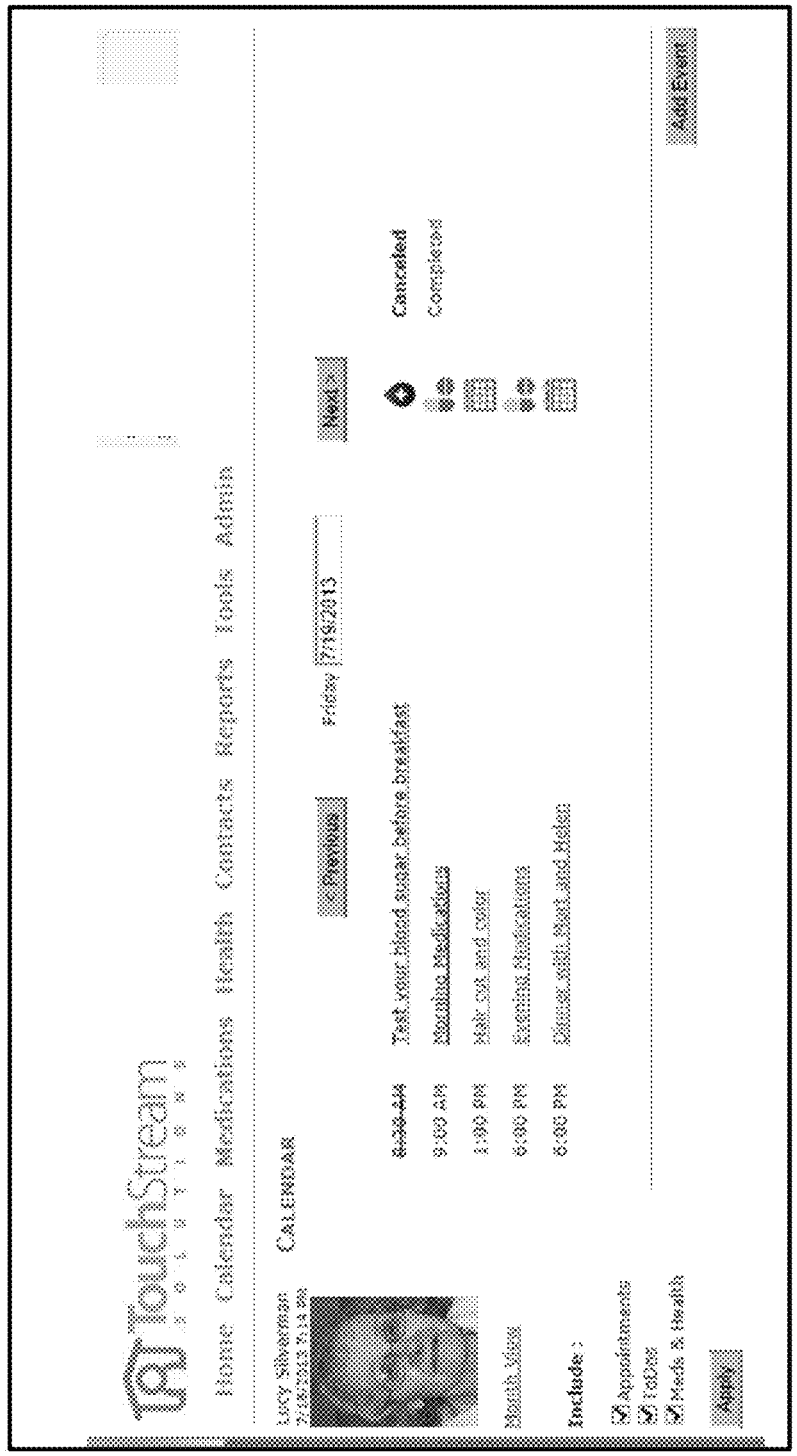

FIG. 6F is an example of a "calendar" user interface screen that may be provided, at least in part, by the system management server 130, and which is configured to display a schedule for a particular home user (e.g., Lucy Silverman) for a particular date (Jul. 19, 2013), according to some embodiments. This schedule may represent the previously discussed activities calendar, and the user interface producing the screen of FIG. 6F may be configured to link to a user interface screen showing all or a portion of the medication schedule generated according to step 415 (e.g., by way of the "morning medications" link or the "evening medications" link), according to some embodiments. The user interface screen of FIG. 6F may be displayed on the caregiver communication device 132 of the caregiver associated with the home user, so that the caregiver can verify or modify the home user's schedule, including the home user's medication schedule. For example, the user interface screen of FIG. 6F may be configured to allow the caregiver to cancel scheduled activities, such as canceling a blood sugar test scheduled for 8:30 am. The user interface screen of FIG. 6F may be configured to allow the caregiver to verify that the home user has taken his or her morning medications, and that there are no scheduled noon-time medications.

In provide medication message step 420 of FIG. 5, the data processing device system 210 or portion thereof of the system management server 130 or the digital companion device 10 is configured to cause the input-output device system 220 or portion thereof to output to the digital companion device 10, one or more messages, according to some embodiments. The messages may include (a) one or more messages pertaining to activities of the activity schedule, (b) one or more medication messages, or both (a) and (b). A medication message may identify a particular medication set from the medication schedule to be taken at a particular time period (e.g., such as an immediately upcoming time period of the time periods in the medication schedule). In some embodiments, the medication message is provided when the current time (determined, for example, by real-time clock 21 in central processor 20 in FIG. 2) matches the start time of a medication event in the medication schedule. For example, an evening medication message may be provided when the current time is 6:00 PM, which matches the evening medications start time shown in FIG. 6A. Medication messages may instruct the resident home user to take the multiple unrelated medications of a medication set during the appropriate or associated time window or period, as will be described later in reference to FIG. 7B, which illustrates an example of a medication message. According to some embodiments, the medication messages may include visible messages, such as text, graphic images, video clips, or animations, or may include or additionally include audio information, such as speech, music, or sound effects.

In embodiments where the data representing the medication schedule accommodates multiple home users, as discussed above, the data processing device system 210 or portion thereof of the system management server 130 or the digital companion device 10 is configured to cause the input-output device system 220 or portion thereof to output to the digital companion device 10, one or more medication messages to each of at least two different users. For example, if it is 6:00 PM on Thursday, July 18, and both home user "Lucy" and home user "Bob" have to take medications at that time, a user interface screen like that shown in FIG. 7B may be presented by the display screen 40 of the digital companion device 10 followed by the display of a similar user interface screen like that shown in FIG. 7B, but for home user "Bob". In some embodiments, the digital companion device confirms that the particular user is receiving the message and taking the medication, for example by performing face recognition on an image captured by the digital companion device 10 using a camera in the reader 36. However, the invention is not limited to any particular configuration of providing multiple medication messages to different users.

Figure 7A:
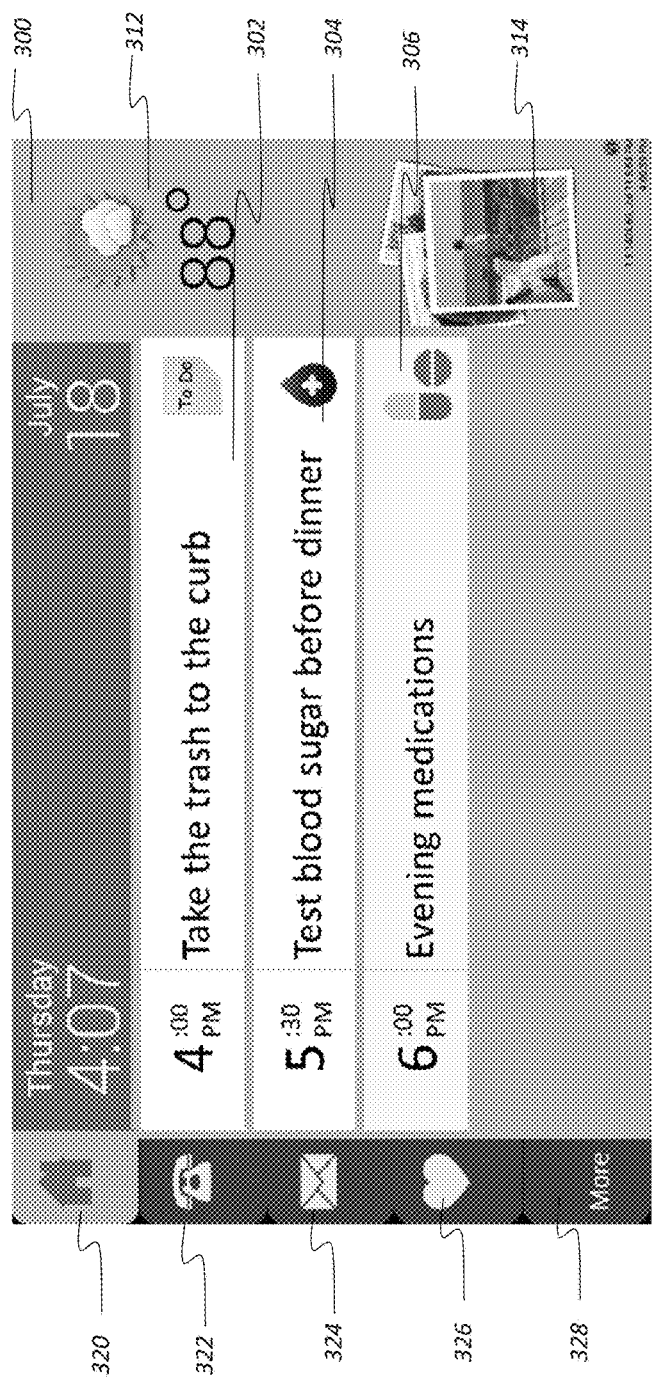

FIG. 7A is an example of a "current schedule" user interface screen 300 for a particular home user (e.g., Lucy) that may be provided, at least in part, by the system management server 130, the digital companion device 10, or both, and which is configured to be displayed on the display screen 40 of the digital companion device 10 located at the residence of the particular home user (e.g., Lucy), according to some embodiments. The interface screen 300 of FIG. 7A illustrates a particular current time of Thursday July 18 at 4:07 pm merely for example. The "current schedule" user interface screen 300 is configured to inform the particular home user (e.g., Lucy) about a scheduled "to do" task 302 (e.g., "4:00 PM—Take the trash to the curb"), which may be part of the previously discussed activities calendar, as well as a scheduled medical related monitoring activity 304 (e.g., "5:30 PM—Test blood sugar before dinner") and a scheduled medication event 306 (e.g., "6:00 PM—Evening medications").

According to some embodiments, the "evening schedule" user interface screen 300 in FIG. 7A is configured to display the current weather conditions 312 (e.g., 88 degrees and cloudy) in the upper right corner, as well as a pictures icon 314 in the lower left corner which, when selected by the home user, permits the home user to view pictures and videos which have been shared with the home user by their caregiver, as well as other relatives and friends who have been granted access to share content with the home user by the system management server 130.

According to some embodiments, the "evening schedule" user interface screen 300 in FIG. 7A displays a number of icons along the left side, including a "home" icon 320, a "phone" icon 322, an "email" icon 324, a "heart" icon 326, and a "more" icon 328. The phone icon 322 may be selected by the home user in order to place a phone call using the digital companion device 10, for example using internet telephony. The email icon 324 may be selected by the home user in order to read email messages sent by others, or send email messages, using the digital companion device 10. The heart icon 326 may be selected by the user in order to lists chronic health items associated with the home user. According to some embodiments, selection of the heart icon 326 enables the home user to record, for example, a blood pressure reading at any time, whether or not a reading is scheduled at the current time If the health activity (e.g., blood pressure reading) is performed during a time when it is scheduled, the digital companion device 10 will associate the health event (e.g., measured blood pressure) with the scheduled event, according to some embodiments.

The more icon 328 may be selected by the user in order to access other features provided by the digital companion device 10. For example, in some embodiments the more icon 328 may be selected by the user in order to listen to favorite music or other recorded programs using the digital companion device 10. The home icon 320 may be selected by the user in order to return to the "current schedule" user interface screen (which is currently being displayed in FIG. 7A), after another one of the icons 322, 324, 326, or 328 has been selected.

FIG. 7B is an example of an "evening medications reminder" user interface screen 330 for a particular home user 334 (e.g., Lucy) that may be provided, at least in part, by the system management server 130, the digital companion device 10, or both, and which is configured to be displayed on the display screen 40 of the digital companion device 10 located at the residence of the particular home user (e.g., Lucy), according to some embodiments. The interface screen 300 of FIG. 7B presents a portion of the medication schedule generated according to step 415. In this regard, in some embodiments, the data processing device system 210 or portion thereof of the system management server 130 may be configured to transmit, via a network (e.g., the Internet 120) and a network interface of the input-output device system 220 or portion thereof of the system management server 130, at least a portion of the medication schedule to a remote device (e.g., digital companion device 10). In some embodiments, the at least the portion of the medication schedule received by the remote device (e.g., digital companion in device 10) facilitates display of a user interface screen like FIG. 7B.

The interface screen 300 of FIG. 7A illustrates a particular current time of Thursday July 18 at 6:00 pm merely for example. The "evening medications reminder" user interface screen 330 may be configured to provide a medication message 332 to the user 334 which identifies one of the plurality of medication containers (e.g., the Thursday PM container 82 in FIG. 8A) which should be removed from the medication container assembly 80 (FIG. 8A) and positioned so that the identification code (e.g., 92 in FIG. 8B) can be read by the reader 36 of the digital companion device 10.

The example "evening medications reminder" user interface screen 330 instructs the home user (e.g., Lucy) to take a medication set of three different unrelated medications, (e.g., a Metformin medication 336A, a Tylenol medication 336B, and a Calcium Carbonate medication 336C) during the current "evening medication" event time period (e.g., 6:00-6:30). This example also provides instructions on how the medications should be taken (e.g., "Do not crush or chew the tablet" for the Metformin medication 336A) and dosing instructions (e.g., "1 Capsule" "500 mg" for the Tylenol medication 336B).

It will be understood that the medications 336A, 336B, and 336C included in the "evening medications reminder" user interface screen 330 are obtained from the medication schedule described earlier in relation to create medication schedule step 415, which was created responsive to the medications which were input by the caregiver as described earlier in relation to create medication pattern step 410, which are listed in the Thu Evening box of the "pillbox view" user interface screen shown in FIG. 6E. It will be further understood that in some embodiments, the medication schedule may be stored in a memory in the digital companion device 10 in FIG. 2, such as in non-volatile storage 22 and in some embodiments, the medication schedule may be stored in a storage memory provided in a network accessible storage system, such as a hard disk drive or other memory attached to the system management server 130 in FIG. 4.

As discussed above, in provide medication message step 420 of FIG. 5, the digital companion device 10 (i.e., the data processing device system 210 thereof, e.g., central processor 20) is configured to cause its input-output device system to output (220 in FIG. 1, e.g., display screen 40 or speakers 44) to output a medication message (e.g., all or a portion of FIG. 7B) which identifies a particular medication set of the plurality of medication sets to be taken at a particular time period of a plurality of time periods of the medication schedule, as well as medication dosing instructions (e.g., 500 mg of Metformin). In the example of FIG. 7B, the medication set may be all of the medications 336A, 336B, 336C, or a subset of those medications, depending upon the embodiment. It will be understood that the medications are not limited to pills, but can include, for example, injections, liquids, creams, lotions, drops, and medication patches. The dosing instructions can provide specific instructions describing, for example, how much medication should be consumed (e.g. 1 tablespoon of a liquid), or where a cream or medication patch should be applied.

In identify medication container step 425 of FIG. 5, the system management server 130 (i.e., the data processing device system 210 thereof) or the digital companion device 10 (i.e., the data processing device system 210 thereof) is configured to receive (e.g., via the input-output-device system 220) an input identification code, e.g., from the reader 36 of the digital companion device 10, according to some embodiments. In some embodiments, the reader 36 reads the identification code associated with a medication set. For example, the identification code may be an RFID tag, a bar code (e.g., 92 in FIG. 8B) or other indicia, or a magnetic strip, as described earlier in relation to FIG. 2 on or integrally formed with a medication container containing the medication set. It will be understood that the digital companion device 10 may be configured to instruct the home user concerning how to position the medication container (e.g., 104 in FIG. 4 or 90 in FIG. 8B) so that the identification code can be properly read by the reader 36 of the digital companion device 10.

In "correct container?" test 430 in FIG. 5, the system management server 130 (i.e., the data processing device system 210 thereof) or the digital companion device 10 (i.e., the data processing device system 210 (e.g., central processor 20) thereof) is configured to determine (e.g., via the input-output-device system 220) whether the input identification code corresponds to the particular medication set (identified by the medication message from step 420) based upon an analysis of at least a portion of the medication schedule and the input identification code from step 425, according to some embodiments. For example, if the input identification code matches an identification code previously stored in association with the particular medication set in the medication schedule (e.g., in non-volatile storage 22 in FIG. 2), it is determined that the user has selected the correct medication set that needs to be taken at that time at step 430, according to some embodiments. In this case, a confirmation message indicating that the correct medication set has been selected by the user may be presented (e.g., by display 40 or audio speaker(s) 44) at step 440.

In some embodiments, this confirmation message is provided using displayed text or an audio message, which indicates the name of the medication container selected (e.g., "Correct—Thursday PM", or "Correct—Metformin"). In some embodiments, the confirmation message also provides dosing instructions. For example, if the medication was provided in the form of eye drops, the dosing instructions could remind the home user of which eye(s) should receive drops, and how many drops to use. As a second example, if the medication was provided in the form of a cream, the dosing instructions could remind the home user where to apply the cream, and how much cream to apply.

In some embodiments, the user interface screen of FIG. 7D is configured to allow a user (the home user or a caregiver) to provide manual confirmation that the home user has taken the medication or medications due to be taken in the present time window. The embodiments of FIG. 7D show one example of this manual confirmation with the "I Did It" button, where the user selects such button to provide an indication that the user has taken the required medication or medications. However, the invention is not limited to any particular technique for providing such manual confirmation. When the user provides such manual confirmation, the data processing device system 210 (e.g., the central processor 20) of the digital companion device 10 receives the input confirmation indicating that a particular medication set has been taken by the home user.

In some embodiments, the data processing device system 210 (e.g., the central processor 20) of the digital companion device 10 is configured to then track the home user's taking of the particular medication set along with earlier-tracked medication sets taken by the home user. The tracking of medication sets taken by a home user may be performed using the data that represents the medication schedule, such that the data that represents the medication schedule may include one or more additional data fields that allow tracking of medication sets taken as well as respective dosages taken and at what time or times. In this regard, the data processing device system 210 (e.g., the central processor 20) of the digital companion device 10 is configured to modify the data that represents the medication schedule to account for the input confirmation (e.g., from the selecting of the "I Did It" button in FIG. 7D).

In some embodiments, this tracking is performed at least in part by the system management server 130. In this regard, the data processing device system 210 (e.g., the central processor 20) of the digital companion device 10 may be configured to transmit, via the network interface 34 and the Internet 120 to the system management server 130, the input confirmation, which provides the system management server 130 with an indication of the home user taking the required medication set (e.g., shown in whole or part in FIG. 7D), which may be in accordance with the at least a portion of the medication schedule transmitted by the system management server 130 to the digital companion device 10 (e.g., to form the interface screen of FIG. 7D). When the system management server 130 tracks or records the medication sets taken by the home user, the caregiver or caregivers for that home user may view such information that the respective caregiver communication devices 132 to understand if the home user is properly taking his or her medications.

In this regard, in some embodiments, the input-confirmation transmitted from the digital companion device 10 to the system management server 130 is forwarded or otherwise provided by the digital companion device 10 or the system management server 130 to one or more caregiver communication devices 132 to inform the caregiver that the home user has taken the required medication set.

Returning to the user interface screen of FIG. 7D, such screen shows, for example, that the home user took his or her Thursday evening medications at 6:15 PM. The home user may press the "close" icon shown in FIG. 7D in order to return to the current schedule display screen, such as an updated version of the current schedule user interface screen shown in FIG. 7A. As discussed above, in some embodiments, the medication schedule data stored in a processor-accessible memory device system 230 (such as non-volatile storage 22) is updated to indicate that the user has selected, taken, or selected and taken the correct medication.

In some embodiments, a home user may take an unscheduled "on-demand" medication, such as a pain-relieving medication that a home user is instructed to take as needed. Typically, such medications have an allowable maximum dosage within a time period. In this regard, the data processing device system 210 or portion thereof of the system management server 130 or the digital companion device 10 may be configured to track on-demand medications taken by the home user to ensure that he or she does not exceed the allowable maximum dosage within the time period. For example, in some embodiments, the data processing device system 210 or portion thereof of the system management server 130 or the digital companion device 10 is configured to receive, via the input-output device system 220 or portion thereof (e.g., reader 36), an input identification code determined to correspond to an on-demand medication. In response to the determination that the input identification code corresponds to the on-demand medication, such data processing device system 210 or portion thereof may be configured to output dosing instructions for the on-demand medication, optionally in light of tracked earlier dosages of the on-demand medication taken by the user within a time period. For example, assume that the on-demand medication is ibuprofen (with respective 200 mg tablets), and the maximum recommended dosage within a day (an example of the time period) is 2,400 mg (or 12 tablets). Also assume that the home user has already taken 6 tablets in 12 hours within the day. In this case, the dosing instructions may indicate that the home user should take no more than 2 tablets at the present time and no more than 6 tablets within the next 12 hours.

In some embodiments, the data processing device system 210 or portion thereof of the system management server 130 or the digital companion device 10 is configured to receive, via the input-output device system 220 or portion thereof, input confirmation indicating that the on-demand medication has been taken by the home user (e.g., by a button such as the "I Did It" button shown in FIG. 7D). In response to receiving this input confirmation, the data processing device system 210 or portion thereof of the system management server 130 or the digital companion device 10 may be configured to store an indication of the on-demand medication, a present dosage taken by the home user, and a time at which the present dosage of the on-demand medication was taken by the user. Such a configuration allows tracking of the on-demand medications and respective dosages taken for later viewing, e.g., by the caregiver, the home user, or a physician. Such a configuration also facilitates prevention of the home user taking access dosages of the on-demand medication.

In this regard, the data processing device system 210 or portion thereof of the system management server 130 or the digital companion device 10 may be configured to retrieve earlier dosages of the on-demand medication taken by the user within a time period; and determine whether the earlier dosages of the on-demand medication taken by the user, if taken with an additional present dosage of the on-demand medication within the time period, would exceed a maximum dosage. If so, the data processing device system 210 or portion thereof of the system management server 130 or the digital companion device 10 may be configured to output a warning message indicating access medication dosage. The warning message may be output to the display screen 40 of the digital companion device 10, to the speakers 44 of the digital companion device 10, to the system management server 130, to a caregiver communication device 132, or a combination of any or all of these devices. For instance, following the above ibuprofen example, if the home-user scanned in an identification code associated with ibuprofen to indicate that the home user would like to take an additional present dose of ibuprofen two hours after taking the previous dose of ibuprofen, the digital companion device 10 may output a message indicating that the home user must wait two more hours before taking the additional present those.

If the input identification code does not correspond to the previously stored identification code associated with the particular medication set at step 430, it is determined that the user has selected an incorrect medication set, according to some embodiments. In this case, at step 435 according to some embodiments, the system management server 130 (i.e., the data processing device system 210 thereof) or the digital companion device 10 (i.e., the data processing device system 210 thereof) may be configured to output (e.g., via the input-output-device system 220) a warning (e.g., by display 40 or audio speaker(s) 44). For example, the "incorrect container" warning message may warn the user that an incorrect medication container has been selected, and indicate which medication container should be used. In some embodiments, the data stored in the storage memory for the particular home user (such as non-volatile storage 22) is updated to indicate that the user has failed to select the correct medication container.

Figure 7C:
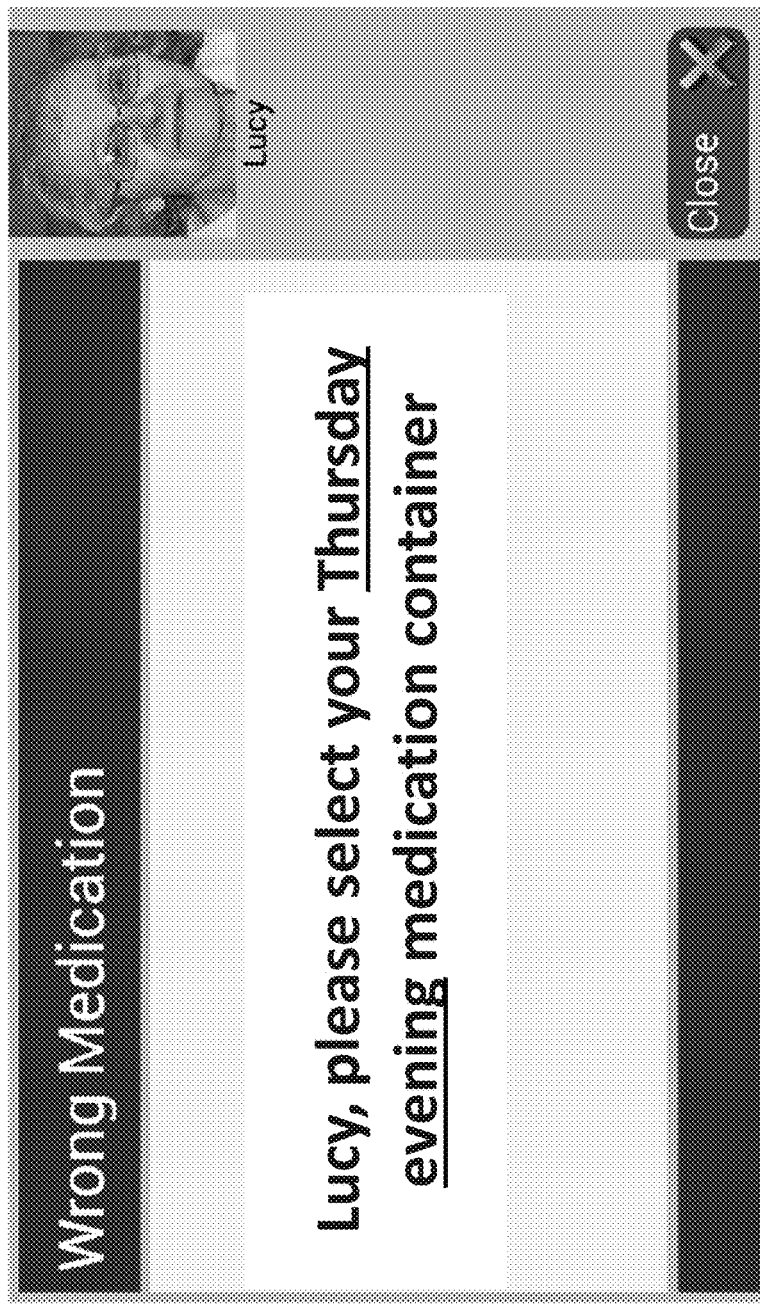

FIG. 7C depicts an example of a warning message user interface screen for a particular home user (e.g., Lucy) which is displayed on the display screen 40 of the digital companion device 10 located at the residence of the particular home user, according to some embodiments. The warning message warns the home user that the wrong medication container has been selected, and instructs the user to select the proper container (e.g., the Thursday evening container 82). In some embodiments, the warning message may include an audio warning or a visually varying warning (e.g., a flashing red light).

In some embodiments, in response to it being determined that the input identification code does not correspond to the previously stored identification code associated with the particular medication set at step 430, the data processing device system 230 or portion thereof (e.g., central processor 20) of the digital companion device 10 is configured to determine whether the input identification code is associated with another home user based upon an analysis of the data representing the medication schedule. For example, assume that a portion of the medication schedule data appears as shown in Table I below:

TABLE I

| User | Medication Name | Identification Code |
|---|---|---|
| Lucy | Metformin | 129528 |
| Lucy | Tylenol | 564816 |
| Lucy | Calcium Carbonate | 816305 |
| Bob | Iron | 162554 |

(It should be noted that the medication schedule would include additional data than that shown in Table I, including additional medications for Lucy as shown in FIG. 6E and additional data fields (columns) as shown in FIG. 6C. In addition, it should be noted that the medication schedule need not be represented as a two-dimensional table, and the invention is not limited to any particular data structure for storing or representing the medication schedule.) In the example of Table I, if the digital companion device 10 (i.e., the data processing device system thereof) is expecting to receive an identification code associated with Lucy (e.g., any of codes 129528, 564816, 816305), but instead receives input identification code 162554, the digital companion device 10 (i.e., the data processing device system thereof) may be configured to not only determine that the input identification code does not correspond to an expected medication set associated with user "Lucy", but also to determine that the input identification code corresponds to a different user, in this example, "Bob". In this situation, the digital companion device 10 may be configured to output a message indicating an incorrect user, such as, e.g., by presenting a visual, audio, or visual and audio message that Lucy may have improperly selected Bob's medication.

In some embodiments, in response to it being determined that the input identification code does not correspond to the previously stored identification code associated with the particular medication set at step 430, the data processing device system 230 or portion thereof (e.g., central processor 20) of the digital companion device 10 is configured to transmit, via a network (e.g., Internet 120) and a network interface (e.g., 34), a warning message to a remote device (e.g., caregiver communication device 132, either directly or via the system management server 130). Such a configuration allows a caregiver to be notified when the home user has selected an incorrect medication set. In some embodiments, this morning message may be an e-mail, SMS message, phone call, or any other type of electronic communication. In this regard, in some embodiments, in response to its being determined that the input identification code does not correspond to the previously stored identification code associated with the particular medication set at step 430, the data processing device system 230 or portion thereof (e.g., central processor 20) of the digital companion device 10 is configured to establish, via a network (e.g., Internet 120) and a network interface (e.g., 34), a communicative connection with a remote device (e.g., caregiver communication device 132, either directly or via the system management server 130). In some embodiments, the communicative connection establishes a videoconference or phone call with a caregiver, which may allow the caregiver to help the home user select the proper medication.

After providing the warning message in provide warning message step 435, the process returns to identify medication container step 425, to determine if the home use has selected another medication container, according to some embodiments. In some embodiments, if the home user repeatedly fails to select the correct container (e.g., if "correct container?" test 430 provides several (e.g., 3 or more) "no" responses) a message may be sent to the caregiver communication device(s) 132 associated with the caregiver associated with the particular home user, to inform the caregiver that the home user has been unable to select the proper medication container. This permits the caregiver to provide assistance to the home user, via videoconference or phone call as described above, or in person, as necessary.

It will be understood in some embodiments, medications for the home user are stored in individual containers, as described earlier in reference to FIG. 8B. In such embodiments, provide medication message step 420, identify medication container step 425, and "correct container?" test 430 may be repeated multiple times, once for each different medication to be taken by the home user during the current medication event (e.g., three times for the three different medications 336A, 336B, and 336C in the example shown in FIG. 7B.)

It will be understood that in some embodiments, the digital companion device 10 may be configured to provide medication management for two or more different users. In this situation, the storage memory (such as non-volatile storage 22) stores data which identifies at least two different users and a plurality of medications to be taken by the two different users according particular schedules for the two different users. In this situation, the digital companion device 10 provides different medication messages to each of the users. The medication messages may include the name or photo of the different users, as described earlier.

It will be understood that in some embodiments, rather than using a medication identifier on a medication container, the digital companion device 10 may be configured to identify the medication by capturing and analyzing an image of the actual medication. The medication may be identified, for example, by analyzing the size, color, shape, or identification codes on the medication.

The invention has been described in detail with particular reference to certain exemplary embodiments thereof. It will, however, be understood that variations and modifications may be effected within the scope of the invention. The present specification and figures are accordingly to be regarded as illustrative rather than restrictive.

Subsets or combinations of various embodiments described above provide further embodiments. These and other changes can be made to the invention in light of the above-detailed description and still fall within the scope of the present invention. In general, in the following claims, the terms used should not be construed to limit the invention to the specific embodiments disclosed in the specification and the claims. Accordingly, the invention is not limited by the disclosure, but instead its scope is to be determined entirely by the following claims.

What is claimed is:

1. A medication management system comprising:
  a first medication container assembly including a first plurality of individual medication containers, the first plurality of individual medication containers configured to retain a first plurality of medication sets, the first medication container assembly associated with a first patient, the first plurality of individual medication containers respectively including a first plurality of computer-readable identification codes, each individual medication container of the first plurality of individual medication containers including a respective computer-readable identification code of the first plurality of computer-readable identification codes that is different than every other computer-readable identification code of the first plurality of computer-readable identification codes, each individual medication container of the first plurality of individual medication containers configured to retain a respective medication set of the first plurality of medication sets, and each medication set of at least one medication set of the first plurality of medication sets includes a respective group of different types of medications;

a second medication container assembly including a second plurality of individual medication containers, the second plurality of individual medication containers configured to retain a second plurality of medication sets, the second medication container assembly associated with a second patient, the second plurality of individual medication containers of the second medication container assembly respectively including a second plurality of computer-readable identification codes, each individual medication container of the second plurality of individual medication containers including a respective computer-readable identification code of the second plurality of computer-readable identification codes that is different than every other computer-readable identification code of the second plurality of computer-readable identification codes, the second plurality of computer-readable identification codes mutually exclusive with the first plurality of computer-readable identification codes of the first medication container assembly, and each individual medication container of the second plurality of individual medication containers configured to retain a respective medication set of the second plurality of medication sets; and a computer system physically distinct from the first medication container assembly and the second medication container assembly and comprising an input-output device system, a processor-accessible memory device system storing a program, and a data processing device system communicatively connected to the processor-accessible memory device system and the input-output device system, wherein the data processing device system is configured by the program at least to:

receive a first input identification code via the input-output device system;

determine that the first input identification code is improper based at least on a comparison of the first input identification code with an expected identification code, the expected identification code selected from at least the first plurality of computer-readable identification codes from the first plurality of individual medication containers of the first medication container assembly; and cause the input-output device system to output a warning in response to it being determined that the first input identification code is improper.

2. The medication management system of claim 1, wherein the data processing device system is configured by the program at least to store, in the processor-accessible memory device system, the first plurality of computer-readable identification codes respectively in association with a first plurality of medication taking events and respectively in association with the first plurality of medication sets.

3. The medication management system of claim 2, wherein each medication taking event of the first plurality of medication taking events is different than every other medication taking event of the first plurality of medication taking events, and wherein the first plurality of medication taking events respectively are associated with the first plurality of medication sets, which are respectively associated with the first plurality of individual medication containers.

4. The medication management system of claim 3, wherein the data processing device system is configured by the program at least to store, in the processor-accessible memory device system, the second plurality of computer-readable identification codes respectively in association with a second plurality of medication taking events and respectively in association with the second plurality of medication sets.

5. The medication management system of claim 4, wherein each medication taking event of the second plurality of medication taking events is different than every other medication taking event of the second plurality of medication taking events, and wherein the second plurality of medication taking events respectively are associated with the second plurality of medication sets, which are respectively associated with the second plurality of individual medication containers.

6. The medication management system of claim 2, wherein the data processing device system is configured by the program at least to store, in the processor-accessible memory device system, the second plurality of computer-readable identification codes respectively in association with a second plurality of medication taking events and respectively in association with the second plurality of medication sets.

7. The medication management system of claim 2, wherein the data processing device system is configured by the program at least to associate, in the processor-accessible memory device system, the respective group of different types of medications in the processor-accessible memory device system with a single respective computer-readable identification code associated with a respective individual medication container configured to retain the respective group of different types of medications, the single respective computer-readable identification code being from the first plurality of computer-readable identification codes, and the respective individual medication container being from the first plurality of individual medication containers.

8. The medication management system of claim 2, wherein each individual medication container of the first plurality of individual medication containers is associated with a time window within a 24-hour period, each time window associated in the processor-accessible memory device system with a respective medication taking event of the first plurality of medication taking events, as well as a start time and an end time.

9. The medication management system of claim 2, wherein the data processing device system is configured by the program at least to store, in the processor-accessible memory device system, a first medication taking event of the first plurality of medication taking events in association with a first dosage of a first medication, and to store, in the processor-accessible memory device system, a second medication taking event of the first plurality of medication taking events in association with a second dosage of the first medication.

10. The medication management system of claim 1, wherein the data processing device system is configured by the program at least to store, in the processor-accessible memory device system and in a state in which at least two medication sets of the first plurality of medication sets include an identical medication, different computer-readable identification codes of the first plurality of computer-readable identification codes in association with the at least two medication sets of the first plurality of medication sets, respectively.

11. The medication management system of claim 1, wherein the data processing device system is configured by the program at least to:
   receive, via the input-output device system, computer-readable identification credentials associated with an identification badge and a caregiver; and
   store, in response to receiving the computer-readable identification credentials, information in the processor-accessible memory device system confirming medical attention provided on a particular day and time by the caregiver.

12. The medication management system of claim 1, wherein the data processing device system is configured by the program at least to transmit, in response to it being determined that the first input identification code is improper, a message to a remote caregiver computer system indicating that a medication taking event has failed.

13. The medication management system of claim 1, wherein the data processing device system is configured by the program at least to:
   receive, via the input-output device system, a second input identification code;
   determine that the second input identification code corresponds to an on-demand medication; and
   receive input confirmation, via the input-output device system and in response to it being determined that the second input identification code corresponds to the on-demand medication, the input confirmation indicating that the on-demand medication has been taken.

14. The medication management system of claim 13, wherein the data processing device system is configured by the program at least to store, in the processor-accessible memory device system, an indication of the on-demand medication, a present dosage taken of the on-demand medication, and a time at which the present dosage of the on-demand medication was taken, in response to receiving the input confirmation.

15. The medication management system of claim 1, wherein the data processing device system is configured by the program at least to:
   receive, via the input-output device system, a second input identification code;
   determine that the second input identification code corresponds to an on-demand medication;
   determine that a maximum dosage of the on-demand medication within a time period would be exceeded; and
   cause the input-output device system to output a warning message in response to it being determined that the maximum dosage of the on-demand medication within the time period would be exceeded.

16. The medication management system of claim 1,
   wherein the processor-accessible memory device system associates a first medication container of the first plurality of individual medication containers with a first time window of a first type on a first day of a week, and associates a second medication container of the first plurality of individual medication containers with a second time window of the first type on a second day of the week, the second day of the week different than the first day of the week,
   wherein the processor-accessible memory device system associates the first time window of the first type on the first day of the week with a first period of time within a 24-hour period, and
   wherein the processor-accessible memory device system associates the second time window of the first type on the second day of the week with a second period of time within a 24-hour period, the second period of time different than the first period of time.

17. The medication management system of claim 16, wherein the first type is a morning time window type or an evening time window type.

* * * * *